(12) United States Patent
Guillo et al.

(10) Patent No.: US 9,856,257 B2
(45) Date of Patent: Jan. 2, 2018

(54) PYRAZOLONAPHTHYRIDINONE DERIVATIVES AS METAP2 INHIBITORS (METHIONINE AMINOPEPTIDASE TYPE-2)

(71) Applicant: SANOFI, Paris (FR)

(72) Inventors: Nathalie Guillo, Paris (FR); Valérie Martin, Paris (FR)

(73) Assignee: SANOFI, Paris (FR)

( * ) Notice: Subject to any disclaimer, the term of this patent is extended or adjusted under 35 U.S.C. 154(b) by 25 days.

(21) Appl. No.: 14/778,948

(22) PCT Filed: Mar. 21, 2014

(86) PCT No.: PCT/EP2014/055719
§ 371 (c)(1),
(2) Date: Sep. 21, 2015

(87) PCT Pub. No.: WO2014/154586
PCT Pub. Date: Oct. 2, 2014

(65) Prior Publication Data
US 2016/0060265 A1  Mar. 3, 2016

(30) Foreign Application Priority Data

Mar. 25, 2013 (EP) ..................................... 13305365

(51) Int. Cl.
C07D 471/14 (2006.01)
C07D 401/12 (2006.01)
C07D 405/14 (2006.01)
C07F 5/04 (2006.01)

(52) U.S. Cl.
CPC ......... *C07D 471/14* (2013.01); *C07D 401/12* (2013.01); *C07D 405/14* (2013.01); *C07F 5/04* (2013.01)

(58) Field of Classification Search
CPC ... C07D 471/14; C07D 401/12; C07D 405/14
USPC ........................................................ 546/79
See application file for complete search history.

(56) References Cited

U.S. PATENT DOCUMENTS 9,169,246 B2 10/2015 Benazet et al.
2014/0235616 A1 8/2014 Benazet et al.

FOREIGN PATENT DOCUMENTS

| EP | 1 925 617 A1 | 5/2008 |
|----|---|---|
| EP | 2 573 073 A1 | 3/2013 |
| WO | WO-2009/027393 A2 | 3/2009 |
| WO | WO-2009/027393 A3 | 3/2009 |
| WO | WO-2012/154678 A1 | 11/2012 |

OTHER PUBLICATIONS

Bradshaw, R.A. et al. (Jul. 1998). "N-Terminal Processing: The Methionine Aminopeptidase and $N^\alpha$-Acetyl Transferase Families," *Trends Biochem. Sci.* 23(7):263-267.

Datta, B. et al. (May 1988). "Roles of a 67-kDa Polypeptide in Reversal of Protein Synthesis Inhibition in Heme-Deficient Reticulocyte Lysate," *PNAS* 85:3324-3328.
Datta, B. (2000). "MAPs and POEP of the Roads from Prokaryotic to Eukaryotic Kingdoms," *Biochimie* 82:95-107.
Database Registry CAS No. 848818-60-0. (Apr. 20, 2005), one page.
Database Registry CAS No. 800402-12-4. (Dec. 21, 2004), one page.
Database Registry CAS No. 78607-32-6. (Nov. 16, 1984), one page.
Griffith, E.G. et al. (Jun. 1997). "Methionine Aminopeptidase (Type 2) is the Common Target for Angiogenesis Inhibitors AGM-1470 and Ovalicin," *Chem. Biol.* 4(6):461-471.
Griffith, E.C. et al. (Dec. 22, 1998). "Molecular Recognition of Angiogenesis Inhibitors Fumagillin and Ovalicin by Methionine Aminopeptidase 2," *PNAS* 95(26):15183-15188.
International Search Report dated Apr. 22, 2014, for PCT Application No. PCT/EP2014/055719, filed on Mar. 21, 2014, five pages.
Kimball, S.R. (1999). "Molecules in Focus—Eukaryotic Initiation Factor eIF2," *Int'l J. Biochem. Cell Biology* 31:25-29.
Kruger, E.A. (Jun. 2000). "TNP-470: An Angiogenesis Inhibitor in Clinical Development for Cancer," *Exp. Opinion Invest. Drugs* 9(6):1383-1396.
Li, X. et al. (Oct. 3, 1996). "Evidence that the Human Homologue of a Rat Initiation Factor-2 Associated Protein ($p^{67}$) is a Methionine Aminopeptidase," *Biochem. Biophys. Res. Commun.* 227(1):152-159.
Li, X. et al. (Dec. 19, 1995). "Amino-Terminal Protein Processing in *Saccharomyces cerevisiae* is an Essential Function that Requires Two Distinct Methionine Aminopeptidases," *PNAS* 92(26):12357-12361.
March, J. (1985). *Advanced Organic Chemistry: Reactions, Mechanisms, and Structure*, $3^{rd}$ Edition, Wiley Interscience, pp. 310-316.
Pestova, T.V. et al. (Jun. 19, 2001). "Molecular Mechanisms of Translation Initiation in Eukaryotes," *PNAS* 98(13):7029-7036.
Satchi-Fainaro, R. et al. (Mar. 2004). "Targeting Angiogenesis with a Conjugate of HPMA Copolymer and TNP-470," *Nature Medicine* 10(3):255-261.
Wang, J. et al. (May 6, 2003). "Physiologically Relevant Metal Cofactor for Methionine Aminopeptidase-2 is Manganese," *Biochem.* 42(17):5035-5042.

(Continued)

*Primary Examiner* — Rita Desai
(74) *Attorney, Agent, or Firm* — Morrison & Foerster LLP

(57) ABSTRACT

The invention related to pyrazolonaphthyridinone derivatives of formula (I) to their preparation and to their therapeutic use as selective inhibitors of type 2 methionine aminopeptidase (hMETAP2).

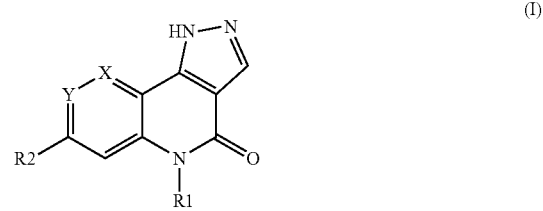

18 Claims, No Drawings

(56) References Cited

OTHER PUBLICATIONS

Wu, Z. et al. (Nov. 30, 2012). "Synthesis and Antifungal Activity of N-(Substituted Pyridinyl)-1-Methyl(Phenyl)-3-(Trifluoromethyl)-1H-Pyrazole-4-Carboxamide Derivatives," *Molecules* 17(12):14205-14218.

Written Opinion of the International Searching Authority dated Apr. 22, 2014, for PCT Application No. PCT/EP2014/055719, filed on Mar. 21, 2014, six pages.

PYRAZOLONAPHTHYRIDINONE DERIVATIVES AS METAP2 INHIBITORS (METHIONINE AMINOPEPTIDASE TYPE-2)

CROSS-REFERENCE TO RELATED APPLICATIONS

This application is a National Phase application under 35 U.S.C §371 of International Application No. PCT/EP2014/055719 filed Mar. 21, 2014, which claims priority benefit to EP Application No. 13305365.2 filed Mar. 25, 2013, the disclosures of which are herein incorporated by reference in their entirety.

The present invention relates to pyrazolonaphthyridinone derivatives, to their preparation and to their therapeutic use.

The compounds according to the present invention are reversible and selective inhibitors of type-2 methionine aminopeptidase (MetAP2).

MetAP2 is an ubiquitous cytosol-based metalloprotease involved in polypeptide catabolism.

MetAP2 catalyses the cleavage of methionine residues located at the N-terminal end of proteins newly synthesized by the cell (Bradshaw R. A. et al., *TIBS,* 1998, 23, 263-267). Cleavage of the N-terminal methionine residues is an important step in the maturation of many proteins and polypeptides. It enables the cell to continue the usual post-translational modifications (myristoylation, palmitoylation, etc.), and then to degrade these same proteins. However, MetAP2 can only cleave this residue on condition that the second residue is of smaller size and uncharged.

MetAP2 is active when the active site contains two divalent metal atoms such as Co(II) or Mn(II) (Li X., Chang Y. H., *Biochem. Biophys. Res. Commun.* 227, 1996, 152-159). Studies have moreover made it possible to establish that human MetAP2 quite probably uses manganese as physiological metal ion (Wang J. et al., *Biochemistry* 2003, 42, 5035-5042).

Another function of MetAP2 is to prevent the protein translation factor eIF2 (eukaryotic initiation factor 2) from phosphorylation(Datta et al., 1988; Li and Chang, 1996). It has been shown that the phosphorylation of eIF2 results in inhibition of overall protein synthesis in eukaryotic cells. By binding to the protein translation factor (eIF2) MetAP2 protects the alpha subunit from inhibitory phosphorylation (Datta, 2000; Kimball, 1999; Pestova et al., 2001). However, inhibitors of MetAP2 activity do not affect the capacity of MetAP2 to block the phosphorylation of eIF2 (Griffith, 1997), which suggests that the two functions are independent.

A MetAP2 isoform exists: MetAP1. These two isoforms are distinguished by the presence of an additional helical domain of about 60 residues within the C-terminal domain of MetAP2. Eukaryotes possess the two forms. A mutation of the two forms is lethal to the eukaryotic cell. This result underlines the interest in identifying inhibitors that are selective towards MetAP2. On the other hand, when only one isoform is mutated, growth reduction is observed (Li X. and Chang Y. H., *Proc. Natl. Acad. Sci.* 1995, 92, 12357-12361). These results confirm that methionine aminopeptidase (MAP) function is essential for cell growth and this activity cannot be relayed by a route independent of MetAPs.

Two types of MetAP2 inhibitor also exist: reversible inhibitors and irreversible inhibitors. Certain known irreversible inhibitors are fumagillin, TNP-470 and ovalicin. At the molecular level, TNP-470, just like fumagillin and ovalicin, binds covalently and irreversibly to MetAP2 (Griffith E. C. et al., *Chem. Biol.* 1997, 4, 461-471).

MetAP2 has been identified as being the target of a family of anti-angiogenic agents derived from fumagillin, described as powerful irreversible MetAP2 inhibitors. The causal link between the inhibition of MetAP2 and the resulting inhibition of endothelial cell proliferation and of neovascularization is clearly established (Griffith E. C. et al., *Chem. Biol.* 1998, 95, 15183-15188).

At the cellular level, the target proteins of MetAP2 are still at the present time very scarcely known. One of them is glyceraldehyde-3-phosphate dehydrogenase. A defect in the synthesis of this enzyme has been observed during treatment of endothelial cells with TNP-470. Recent studies support the hypothesis that the anti-MetAP2 activity of TNP-470 is the source of its anti-angiogenic activity.

It has been shown that irreversible MetAP2 inhibitors play a role in the treatment of pulmonary and hepatic fibroses. Fibrosis is the abnormal formation of scar tissues following a tissue lesion and leads to chronic and progressive impairment of the affected organs, which may result in serious dysfunction of the affected organ. Many causes of fibrosis may exist, but in the majority of cases the cause of the affliction remains unknown and the lesions are difficult to detect. Aggregates of activated fibroblasts and myofibroblasts develop, which constitute the start of numerous fibrotic foci. When the lesions are formed, they are irreversible and cannot be eliminated. Treatments are thus directed towards slowing down the evolution of the complaint and of improving the symptoms. In this context, irreversible MetAP2 inhibitors have shown on in vivo models a reduction of pulmonary and hepatic fibrosis. However, substantial toxicity of these irreversible inhibitors has been demonstrated (Kruger E. A., *Exp. Opinion Invest. Drugs,* 2000; Satchi-Fainaro R. et al., *Nature Medicine,* 2004).

The present invention provides compounds of the formula (I)

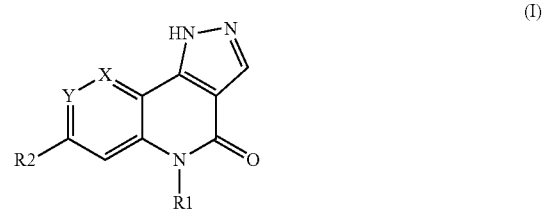

in which:
X represents CH or a nitrogen atom,
Y represents CH or a nitrogen atom, where X or Y is a nitrogen atom,
$R_1$ represents a (C1-C4)alkyl non substituted or substituted with one or more halogen atoms,
$R_2$ represents an aryl or a heteroaryl group, non substituted or substituted with one or more substituents independently selected from:
a halogen atom,
a (C1-C4)alkyl group, where the alkyl group is non substituted or substituted with one or more substituents independently selected from a halogen atom, a heterocyclyl, (C1-C4)alkoxy or hydroxy group or $NHR_3$
$O—R_4$
$(CO)NR_5R_{5'}$,
a heterocyclyl group, non substituted or substituted with one or more (C1-C4)alkyl group a cycloalkyl group
a cyano group
$NR_6R_{6'}$
$SO_2NR_6R_{6'}$
$NHSO_2R_7$
$NH(CO)R_7$
$(CO)R_8$ and
a heteroaryl group, $R_3$ represents a (C1-C4)alkyl or a cycloalkyl group, $R_4$ represents a hydrogen atom or a (C1-C4)alkyl group, where the alkyl group is non substituted or substituted with one or more halogen atom or heterocyclyl group, $R_5$ and $R_{5'}$ represent independently a hydrogen atom, a (C1-C4)alkyl or aryl group, $R_6$ and $R_{6'}$ represent independently a hydrogen atom or a (C1-C4)alkyl group, $R_7$ represents a (C1-C4)alkyl group, and $R_8$ represents a (C1-C4)alkyl, (C1-C4)alkoxy, cycloalkyl or hydroxy group.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may be present as well under tautomer forms and are part of the invention.

The compounds of formula (I) may exist in the form of bases or addition salts with acids or bases, in particular pharmaceutically acceptable salts. Such addition salts form part of the invention.

These salts are advantageously prepared with pharmaceutically acceptable acids, such as hydrochloric acid, but the salts of other acids that are useful, for example, for purifying or isolating the compounds of formula (I) also form part of the invention.

In the context of the present invention, certain terms have the following definitions:
- a halogen atom: a fluorine, a chlorine, a bromine or an iodine atom;
- an alkyl group: a linear or branched saturated aliphatic group. Examples include the groups methyl, ethyl, propyl, isopropyl, etc;
- a cycloalkyl group: a cyclic (C3-C6)alkyl group. Examples include the groups cyclopropyl, cyclobutyl, cyclopentyl, cyclohexyl, etc.;
- an alkoxy group: a radical —O-alkyl in which the alkyl group is as defined above.

Examples of alkoxy group include methoxy, ethoxy, isopropoxy, etc.;
- a cyano group: a group CN;
- a hydroxy group: a group OH;
- an aryl group: a cyclic aromatic group comprising between 5 and 10 carbon atoms. Examples of an aryl group include phenyl group;
- a heteroaryl group: a mono or bicyclic aromatic group comprising between 5 and 10 carbon atoms and comprising between 1 and 5 heteroatoms, such as nitrogen or oxygen. Examples of heteroaryl groups include pyridine, 2-pyridyl, 4-pyridyl, 3-pyridyl, pyrazole, pyrimidine and quinoline groups;
- a heterocyclyl: a non substituted or bridged cyclic alkyl group comprising from 4 to 9 atoms forming this ring, 1 or 2 of which are heteroatoms, such as oxygen or nitrogen. Examples of heterocyclyl groups include pyrrolidine, piperazine, piperidine, morpholine and diazepane groups.

Among the compounds of formula (I) that are subject matter of the invention, a first group of compounds is composed of the compounds for which X represents a nitrogen atom and Y represents CH.

Among the compounds of formula (I) that are subject matter of the invention, a second group of compounds is composed of the compounds for which X represents CH and Y represents a nitrogen atom.

Among the compounds that are subjects of the invention, a third group of compounds is composed of the compounds of formula (I) in which R1 represents a (C1-C4)alkyl group non substituted or substituted with one or more fluorine atoms, more particularly a trifluoroethyl group.

Among the compounds of formula (I) that are subjects of the invention, a fourth group of compounds is composed of the compounds for which R2 represents an aryl group non substituted or substituted with one or more substituents independently selected from:
- a halogen atom
- a $(C_1-C_4)$alkyl group, where the alkyl group is non substituted or substituted with one or more substituents independently selected from a halogen atom, a heterocyclyl, $(C_1-C_4)$alkoxy or hydroxy group or $NHR_3$
- a hydroxy group
- $O—R_{4'}$
- $(CO)NHR_{5'}$
- a heterocyclyl group, non substituted or substituted with a $(C_1-C_4)$alkyl group
- $NR_6R_{6'}$
- $SO_2NR_6R_{6'}$
- $NHSO_2R_{7'}$
- $NH(CO)R_{7'}$
- $(CO)R_8$ and
- a heteroaryl group.

Among the compounds of the fourth group, mention may be made of the compounds of formula (I) for which R2 represents a phenyl group.

Among the compounds of formula (I) that are subjects of the invention, a fifth group of compounds is composed of the compounds for which R2 represents a heteroaryl group non substituted or substituted with one or more substituents independently selected from:
- a halogen atom
- a $(C_1-C_4)$alkyl group, where the alkyl group is non substituted or substituted with one or more substituents independently selected from a halogen atom, a heterocyclyl, $(C_1-C_4)$alkoxy or hydroxy group or $NHR_3$,
- $O—R_4$
- a heterocyclyl group, non substituted or substituted with a $(C_1-C_4)$alkyl group
- a cycloalkyl group
- a cyano group
- $NR_6R_{6'}$ and
- $(CO)R_{8'}$.

Among the compounds of the fifth group, mention may be made of the compounds of formula (I) for which R2 represents a heteroaryl group comprising 1 or 2 nitrogen atoms.

Among the compounds of the latter group, mention may be made of the compounds of formula (I) for which R2 represents a pyridine, a pyrimidine or a quinoline group.

Among the compounds of formula (I) that are subjects matter of the invention, mention may be made in particular of the following compounds:

compound no 1: 7-(2-Chloro-pyridin-3-yl)-5-(2,2,2-trifluoro-ethyl)-1,5-dihydro-pyrazolo[4,3-c][1,6]naphthyridin-4-one compound no 2: 7-Pyridin-2-yl-5-(2,2,2-trifluoro-ethyl)-1,5-dihydro-pyrazolo[4,3-c][1,6]naphthyridin-4-one compound no 3: 7-[2-(4-Methyl-piperazin-1-yl)-pyridin-4-yl]-5-(2,2,2-trifluoro-ethyl)-1,5-dihydro-pyrazolo[4,3-c][1,6]naphthyridin-4-one compound no 4: 7-(4-Fluoro-phenyl)-5-(2,2,2-trifluoro-ethyl)-1,5-dihydro-pyrazolo[4,3-c][1,6]naphthyridin-4-one compound no 5: 7-o-Tolyl-5-(2,2,2-trifluoro-ethyl)-1,5-dihydro-pyrazolo[4,3-c][1,6]naphthyridin-4-one compound no 6: 5-(2,2,2-Trifluoro-ethyl)-7-(2-trifluoromethyl-phenyl)-1,5-dihydro-pyrazolo[4,3-c][1,6]naphthyridin-4-one compound no 7: 7-(2-Fluoro-phenyl)-5-(2,2,2-trifluoro-ethyl)-1,5-dihydro-pyrazolo[4,3-c][1,6]naphthyridin-4-one compound no 8: 7-Pyridin-4-yl-5-(2,2,2-trifluoro-ethyl)-1,5-dihydro-pyrazolo[4,3-c][1,6]naphthyridin-4-one compound no 9: 7-Quinolin-8-yl-5-(2,2,2-trifluoro-ethyl)-1,5-dihydro-pyrazolo[4,3-c][1,6]naphthyridin-4-one compound no 10: 5-(2,2,2-Trifluoro-ethyl)-7-(2-trifluoromethoxy-phenyl)-1,5-dihydro-pyrazolo[4,3-c][1,6]naphthyridin-4-one compound no 11: 2-[4-Oxo-5-(2,2,2-trifluoro-ethyl)-4,5-dihydro-1H-pyrazolo[4,3-c][1,6]naphthyridin-7-yl]benzamide compound no 12: 7-(4-Morpholin-4-yl-phenyl)-5-(2,2,2-trifluoro-ethyl)-1,5-dihydro-pyrazolo[4,3-c][1,6]naphthyridin-4-one compound no 13: 7-(6-Amino-pyridin-3-yl)-5-(2,2,2-trifluoro-ethyl)-1,5-dihydro-pyrazolo[4,3-c][1,6]naphthyridin-4-one compound no 14: 7-(2-Fluoro-4-methoxy-phenyl)-5-(2,2,2-trifluoro-ethyl)-1,5-dihydro-pyrazolo[4,3-c][1,6]naphthyridin-4-one compound no 15: 4-[4-Oxo-5-(2,2,2-trifluoro-ethyl)-4,5-dihydro-1H-pyrazolo[4,3-c][1,6]naphthyridin-7-yl]-N-phenyl-benzamide compound no 16: 2-Fluoro-N-methyl-5-[4-oxo-5-(2,2,2-trifluoro-ethyl)-4,5-dihydro-1H-pyrazolo[4,3-c][1,6]naphthyridin-7-yl]-benzamide compound no 17: 7-(2-Morpholin-4-ylmethyl-phenyl)-5-(2,2,2-trifluoro-ethyl)-1,5-dihydro-pyrazolo[4,3-c][1,6]naphthyridin-4-one compound no 18: 7-(2-Ethoxymethyl-phenyl)-5-(2,2,2-trifluoro-ethyl)-1,5-dihydro-pyrazolo[4,3-c][1,6]naphthyridin-4-one compound no 19: N-Methyl-2-[4-oxo-5-(2,2,2-trifluoro-ethyl)-4,5-dihydro-1H-pyrazolo[4,3-c][1,6]naphthyridin-7-yl]-benzenesulfonamide compound no 20: 7-(3-Chloro-2-hydroxy-phenyl)-5-(2,2,2-trifluoro-ethyl)-1,5-dihydro-pyrazolo[4,3-c][1,6]naphthyridin-4-one compound no 21: 7-[2-(2-Pyrrolidin-1-yl-ethoxy)-phenyl]-5-(2,2,2-trifluoro-ethyl)-1,5-dihydro-pyrazolo[4,3-c][1,6]naphthyridin-4-one compound no 22: N-{2-[4-Oxo-5-(2,2,2-trifluoro-ethyl)-4,5-dihydro-1H-pyrazolo[4,3-c][1,6]naphthyridin-7-yl]-Aphenyl}-methanesulfonamide compound no 23: 7-(3-Pyrazole-1-yl-phenyl)-5-(2,2,2-trifluoro-ethyl)-1,5-dihydro-pyrazolo[4,3-c][1,6]naphthyridin-4-one compound no 24: 7-(6-Chloro-2-methyl-pyridin-3-yl)-5-(2,2,2-trifluoro-ethyl)-1,5-dihydro-pyrazolo[4,3-c][1,6]naphthyridin-4-one compound no 25: N-Isopropyl-4-[4-oxo-5-(2,2,2-trifluoro-ethyl)-4,5-dihydro-1H-pyrazolo[4,3-c][1,6]naphthyridin-7-yl]-benzenesulfonamide compound no 26: 7-(2-isopropoxy-pyridin-4-yl)-5-(2,2,2-trifluoro-ethyl)-1,5-dihydro-pyrazolo[4,3-c][1,6]naphthyridin-4-one compound no 27: 7-(5-Methoxy-pyridin-3-yl)-5-(2,2,2-trifluoro-ethyl)-1,5-dihydro-pyrazolo[4,3-c][1,6]naphthyridin-4-one compound no 28: 7-(2-Ethoxy-pyridin-3-yl)-5-(2,2,2-trifluoro-ethyl)-1,5-dihydro-pyrazolo[4,3-c][1,6]naphthyridin-4-one compound no 29: N,N-Dimethyl-2-[4-oxo-5-(2,2,2-trifluoro-ethyl)-4,5-dihydro-1H-pyrazolo[4,3-c][1,6]naphthyridin-7-yl]-benzenesulfonamide compound no 30: N-Ethyl-4-[4-oxo-5-(2,2,2-trifluoro-ethyl)-4,5-dihydro-1H-pyrazolo[4,3-c][1,6]naphthyridin-7-yl]-benzenesulfonamide compound no 31: 7-[6-(4-Methyl-piperazin-1-yl)-pyridin-3-yl]-5-(2,2,2-trifluoro-ethyl)-1,5-dihydro-pyrazolo[4,3-c][1,6]naphthyridin-4-one compound no 32: 7-(2-Morpholin-4-yl-phenyl)-5-(2,2,2-trifluoro-ethyl)-1,5-dihydro-pyrazolo[4,3-c][1,6]naphthyridin-4-one compound no 33: 7-(2-Pyrrolidin-1-yl-pyridin-3-yl)-5-(2,2,2-trifluoro-ethyl)-1,5-dihydro-pyrazolo[4,3-c][1,6]naphthyridin-4-one compound no 34: 7-(2-[1,4]Diazepan-1-yl-pyridin-3-yl)-5-(2,2,2-trifluoro-ethyl)-1,5-dihydro-pyrazolo[4,3-c][1,6]naphthyridin-4-one compound no 35: 7-[2-(Ethyl-methyl-amino)-pyridin-3-yl]-5-(2,2,2-trifluoro-ethyl)-1,5-dihydro-pyrazolo[4,3-c][1,6]naphthyridin-4-one compound no 36: 7-(2-Fluoro-pyridin-3-yl)-5-(2,2,2-trifluoro-ethyl)-1,5-dihydro-pyrazolo[4,3-c][1,6]naphthyridin-4-one compound no 37: 7-(2-Chloro-pyridin-3-yl)-5-(2,2,2-trifluoro-ethyl)-1,5-dihydro-pyrazolo[4,3-c][1,5]naphthyridin-4-one compound no 38: 7-Pyridin-2-yl-5-(2,2,2-trifluoro-ethyl)-1,5-dihydro-pyrazolo[4,3-c][1,5]naphthyridin-4-one compound no 39: 7-Pyridin-4-yl-5-(2,2,2-trifluoro-ethyl)-1,5-dihydro-pyrazolo[4,3-c][1,5]naphthyridin-4-one compound no 40: 7-[2-(4-Methyl-piperazin-1-yl)-pyridin-4-yl]-5-(2,2,2-trifluoro-ethyl)-1,5-dihydro-pyrazolo[4,3-c][1,5]naphthyridin-4-one compound no 41: 3-[4-Oxo-5-(2,2,2-trifluoro-ethyl)-4,5-dihydro-1H-pyrazolo[4,3-c][1,5]naphthyridin-7-yl]-pyridine-2-carboxylic acid methyl ester compound no 42: 7-(6-Amino-pyridin-2-yl)-5-(2,2,2-trifluoro-ethyl)-1,5-dihydro-pyrazolo[4,3-c][1,5]naphthyridin-4-one compound no 43: 7-(2-Dimethylamino-phenyl)-5-(2,2,2-trifluoro-ethyl)-1,5-dihydro-pyrazolo[4,3-c][1,5]naphthyridin-4-one compound no 44: 5-(2,2,2-Trifluoro-ethyl)-7-(3-trifluoromethyl-pyridin-2-yl)-1,5-dihydro-pyrazolo[4,3-c][1,5]naphthyridin-4-one compound no 45: 5-(2,2,2-Trifluoro-ethyl)-7-(5-trifluoromethyl-pyridin-2-yl)-1,5-dihydro-pyrazolo[4,3-c][1,5]naphthyridin-4-one compound no 46: 3-[4-Oxo-5-(2,2,2-trifluoro-ethyl)-4,5-dihydro-1H-pyrazolo[4,3-c][1,5]naphthyridin-7-yl]-pyridine-2-carbonitrile compound no 47: 7-(2-Cyclopropylaminomethyl-phenyl)-5-(2,2,2-trifluoro-ethyl)-1,5-dihydro-pyrazolo[4,3-c][1,5]naphthyridin-4-one compound no 48: 7-(4-Cyclopentyl-pyrimidin-5-yl)-5-(2,2,2-trifluoro-ethyl)-1,5-dihydro-pyrazolo[4,3-c][1,5]naphthyridin-4-one compound no 49: 7-(5-Chloro-2-methoxy-pyridin-3-yl)-5-(2,2,2-trifluoro-ethyl)-1,5-dihydro-pyrazolo[4,3-c][1,5]naphthyridin-4-one compound no 50: 7-(3-Methylaminomethyl-pyridin-2-yl)-5-(2,2,2-trifluoro-ethyl)-1,5-dihydro-pyrazolo[4,3-c][1,5]naphthyridin-4-one compound no 51: 7-(4-isopropyl-pyrimidin-5-yl)-5-(2,2,2-trifluoro-ethyl)-1,5-dihydro-pyrazolo[4,3-c][1,5]naphthyridin-4-one compound no 52: 7-(5-Chloro-pyridin-2-yl)-5-(2,2,2-trifluoro-ethyl)-1,5-dihydro-pyrazolo[4,3-c][1,5]naphthyridin-4-one compound no 53: 7-(3-Chloro-pyridin-2-yl)-5-(2,2,2-trifluoro-ethyl)-1,5-dihydro-pyrazolo[4,3-c][1,5]naphthyridin-4-one compound no 54: 7-(2-Amino-6-methyl-pyrimidin-4-yl)-5-(2,2,2-trifluoro-ethyl)-1,5-dihydro-pyrazolo[4,3-c][1,5]naphthyridin-4-one compound no 55: 7-(2-Amino-phenyl)-5-(2,2,2-trifluoro-ethyl)-1,5-dihydro-pyrazolo[4,3-c][1,5]naphthyridin-4-one compound no 56: 5-(2,2,2-Trifluoro-ethyl)-7-(4-trifluoromethyl-phenyl)-1,5-dihydro-pyrazolo[4,3-c][1,5]naphthyridin-4-one compound no 57: 7-[2-(2-Hydroxy-ethyl)-phenyl]-5-(2,2,2-trifluoro-ethyl)-1,5-dihydro-pyrazolo[4,3-c][1,5]naphthyridin-4-one compound no 58: 2-[4-Oxo-5-(2,2,2-trifluoro-ethyl)-4,5-dihydro-1H-pyrazolo[4,3-c][1,5]naphthyridin-7-yl]-nicotinonitrile compound no 59: 7-(6-Methyl-pyrimidin-4-yl)-5-(2,2,2-trifluoro-ethyl)-1,5-dihydro-pyrazolo[4,3-c][1,5]naphthyridin-4-one compound no 60: 5-(2,2,2-Trifluoro-ethyl)-7-(6-trifluoromethyl-pyridin-3-yl)-1,5-dihydro-pyrazolo[4,3-c][1,5]naphthyridin-4-one compound no 61: 7-(3-Amino-pyridin-4-yl)-5-(2,2,2-trifluoro-ethyl)-1,5-dihydro-pyrazolo[4,3-c][1,5]naphthyridin-4-one compound no 62: N-{2-[4-Oxo-5-(2,2,2-trifluoro-ethyl)-4,5-dihydro-1H-pyrazolo[4,3-c][1,5]naphthyridin-7-yl]-A-phenyl}-butyramide compound no 63: 7-(4-Cyclohexyl-pyrimidin-5-yl)-5-(2,2,2-trifluoro-ethyl)-1,5-dihydro-pyrazolo[4,3-c][1,5]naphthyridin-4-one compound no 64: N-{2-[4-Oxo-5-(2,2,2-trifluoro-ethyl)-4,5-dihydro-1H-pyrazolo[4,3-c][1,5]naphthyridin-7-yl]-phenyl}-isobutyramide compound no 65: 7-(2-Acetyl-phenyl)-5-(2,2,2-trifluoro-ethyl)-1,5-dihydro-pyrazolo[4,3-c][1,5]naphthyridin-4-one compound no 66: 7-[4-(cyclopropylcarbonyl)phenyl]-5-(2,2,2-trifluoroethyl)-1,5-dihydro-4H-pyrazolo[4,3-c][1,5]naphthyridin-4-one compound no 67: 7-Pyridin-3-yl-5-(2,2,2-trifluoro-ethyl)-1,5-dihydro-pyrazolo[4,3-c][1,5]naphthyridin-4-one compound no 68: 3-[4-Oxo-5-(2,2,2-trifluoro-ethyl)-4,5-dihydro-1H-pyrazolo[4,3-c][1,5]naphthyridin-7-yl]-pyridine-2-carboxylic acid in the form of a base, enantiomers, diastereoisomers, tautomers including racemic mixture, and addition salt with an acid.

In the text below, a protective group PG is a group which makes it possible on one hand to protect a reactive function such as a hydroxyl or an amine during a synthesis and on the other hand allows the reactive function to be restored intact at the end of synthesis. Examples of protective groups and also methods of protection and deprotection are given in "Protective Groups in Organic Synthesis", Greene et al., 4$^{th}$ Edition (John Wiley & Sons, Inc., New York).

A leaving group in the text below is a group that can be readily cleaved from a molecule by breaking a heterolytic bond, with departure of an electron pair. This group may thus be replaced easily by another group during a substitution reaction, for example. Such leaving groups are, for example, halogens or an activated hydroxyl group such as methanesulphonate, benzenesulphonate, p-toluenesulfonate, triflate, acetate, etc. Examples of leaving groups and also references for preparing them are given in "Advanced Organic Chemistry", J. March, 3$^{rd}$ Edition, Wiley Interscience, pp. 310-316.

In accordance with the invention, the compounds of general formula (I) may be prepared according to the processes that follow.

Unless otherwise mentioned, R1 and R2 are as defined previously.

Scheme 1: preparation of the pyrazolonaphthyridinone intermediates of formula (VI)

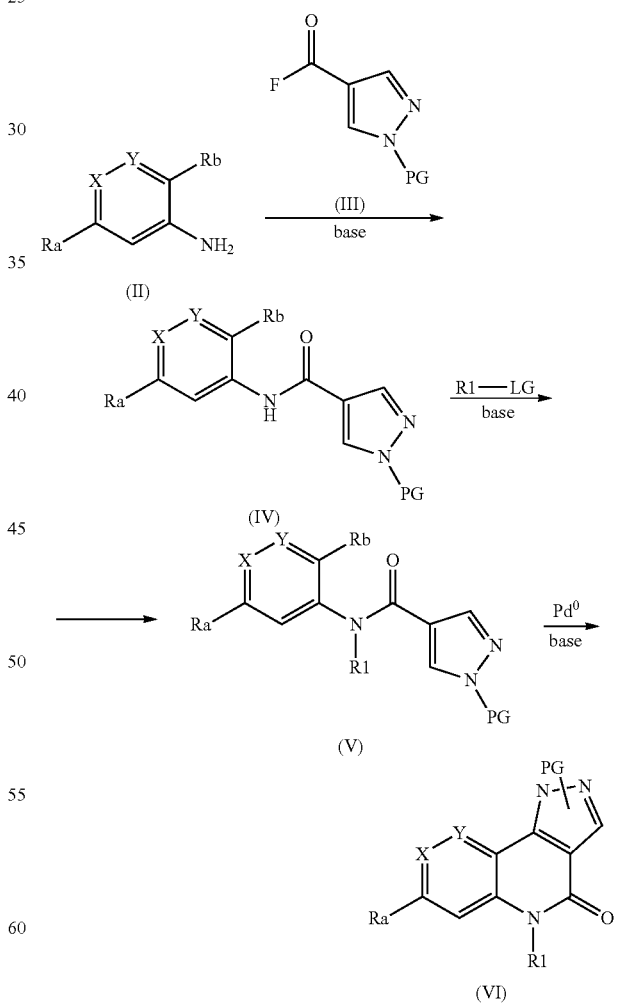

wherein X, Y, R1 and PG are as described above, Ra represents a chlorine or bromine atom, and compounds of formula (II) (IV) (V) and (VI) respectively comprise:

compounds of formula (IIa), (IVa), (Va) and (Via) for which X represents a nitrogen atom, Y represents CH, and Rb represents an iodine atom and compounds of formula (IIIb), (IVb), (Vb) and (VIb) for which X represents CH, Y represents a nitrogen atom, and Rb represents a chlorine, bromine or iodine atom.

Scheme 1 illustrates a chemical route for the synthesis of the compound of formula (VI) from the amino-pyridines of formula (IIa) with Ra being chlorine or bromine and Rb being iodine or from amino-pyridines of formula (IIb) with Ra being chlorine or bromine and Rb being chlorine or bromine or iodine. The amino-pyridines (II) react with an acid fluoride of formula (III) comprising a protecting group on the pyrazole that is stable in basic medium such as SEM or THP in the presence of a base such as tBuOK or NaH in a solvent such as THF or DMF, at room temperature, to give the amide of formula (IV). The amide of formula (IV) may be alkylated with an electrophilic group R1-LG in which LG is a good leaving group such as a halogen or a triflate, in the presence of a base such as NaH, tBuOK, in an inert solvent such as DMF or MeTHF, at room temperature or by heating up to 80° C. The N-alkyl compounds of formulae (Va) and (Vb) are predominantly obtained versus their O-alkyl isomers, and are then engaged in an intramolecular Heck reaction catalysed with palladium, for example with Pd(PPh$_3$)$_4$, in the presence of a weak base such as triethylamine or sodium or potassium acetate, in a solvent such as DMF or NMP, while heating to between 60 and 120° C. to give the protected 1,5-dihydro-4H-pyrazolo[4,3-c][1,6]naphthyridin-4-one of formula (Via) and the protected 1,5-dihydro-4H-pyrazolo[4,3-c][1,5]naphthyridin-4-one of formula (Vib) respectively.

Scheme 2 (route A): Production of the Compounds of Formula (I) from the Intermediates of Formula (VI)

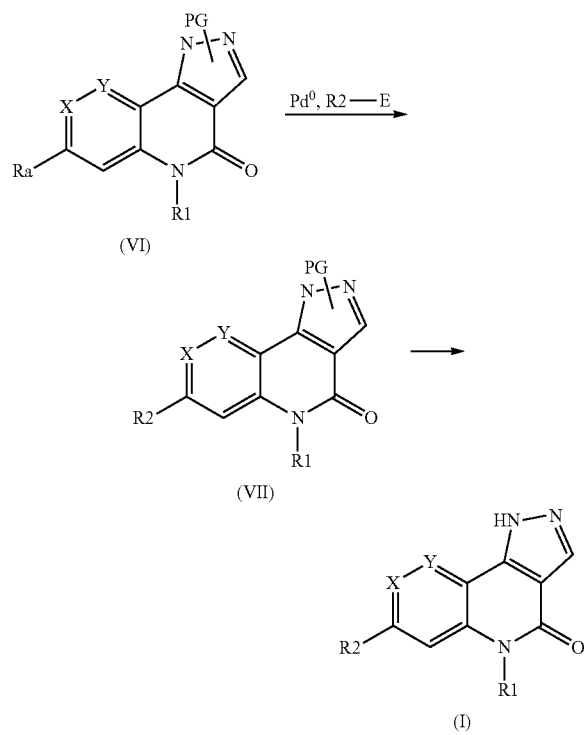

wherein X, Y, R1, Ra and PG are defined as described above.

The halogenated derivative of formula (VI) may be engaged in an organometallic coupling reaction catalysed with palladium, for example PdCl$_2$(dppf), Pd(PPh$_3$)$_4$, Pd(t-Bu$_3$P)$_2$ either with boronic acids or esters or with tin derivatives, in the presence or absence of a phosphine ligand and/or of a weak base such as caesium carbonate or potassium carbonate, in a solvent such as DMF or dioxane or in the presence of water, by heating to between 80 and 150° C., to give the compounds of formula (VII) with R2 being as described previously. Finally, the compounds of formula (I) are obtained after deprotection of the pyrazole of the compounds of formula (VII) under suitable conditions according to the protecting group PG. For example, when PG represents SEM or THP in the compounds of formula (VII), a treatment in acidic medium, for example with TFA or anhydrous dilute HCl, makes it possible to obtain the compounds of formula (I).

Scheme 3 (route B): Alternative to the Preparation of the Compounds of Formula (I) via the Boronic Acid or Ester of Formula (VIII)

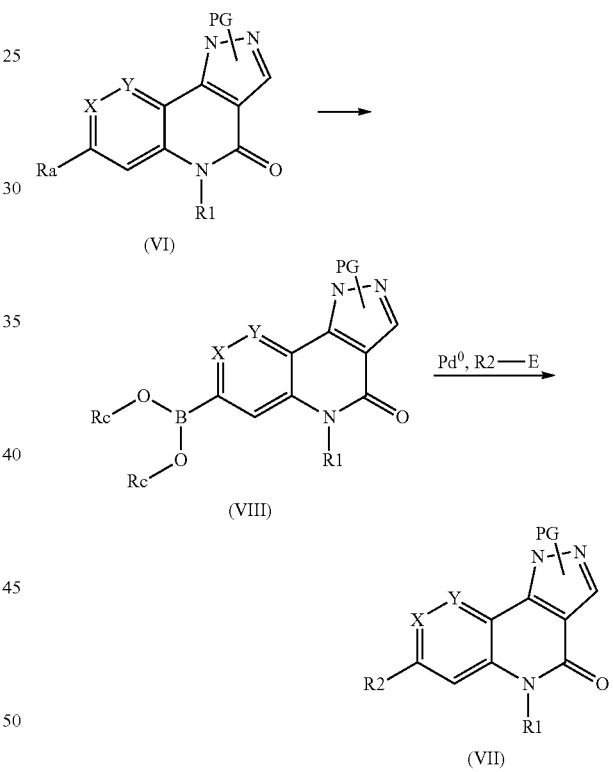

wherein X, Y, R1, Ra and PG are as described above and each Rc represents a hydrogen atom or the two groups Rc are each a carbon atom and are bonded together, and are non substituted or substituted with one or more (C1-C4) alkyl group.

The halogenated derivative of formula (VI) obtained according to the processes described in Scheme 1 may be converted into the boronic acid or ester of formula (VIII), via a palladium-catalysed coupling reaction with for example Pd(dba)$_2$ with a diborane derivative, for example bis(pinacolato)diborane, in the presence of a base such as potassium acetate and in the presence or not of a phosphine ligand. The boronic acid or ester of formula (VIII) may be engaged in a palladium-catalysed Suzuki coupling reaction with aromatic or heteroaromatic substituents R2 bearing a leaving group E such as a halogen atom, for instance chlorine, bromine or iodine or a triflate group, to give the compounds of formula (VII) that allows preparation of the compounds of formula (I) as described previously.

When R2 is an aryl or an heteroaryl group substituted with one halogen atom, that halogen atom may be substituted by a primary or secondary amine in the presence or absence of a palladium(0) or copper(I) catalyst, in the presence or absence of a base, to give the compounds in which R2 is an aryl or a heteroaryl substituted by $NR_6R_{6'}$ or an heterocyclyl group.

In Schemes 1-3, the starting compounds and the reagents, when their preparation method is not described, are commercially available or described in the literature, or else may be prepared according to methods that are described therein or that are known to those skilled in the art.

According to another of its aspects, a subject of the invention is also compounds of formulae (IV). These compounds are useful as intermediates for synthesizing compounds of formula (I).

According to another of its aspects, a subject of the invention is also compounds of formulae (V). These compounds are useful as intermediates for synthesizing compounds of formula (I).

According to another of its aspects, a subject of the invention is also compounds of formulae (VI). These compounds are useful as intermediates for synthesizing compounds of formula (I).

According to another of its aspects, a subject of the invention is also compounds of formulae (VII). These compounds are useful as intermediates for synthesizing compounds of formula (I).

According to another of its aspects, a subject of the invention is also compounds of formulae (VIII). These compounds are useful as intermediates for synthesizing compounds of formula (I).

The examples that follow describe the preparation of certain compounds in accordance with the invention. The examples are not limiting, but serve merely to illustrate the present invention. The table herein below illustrates the chemical structures and physical properties of a number of compounds according to the invention.

The following abbreviations and empirical formulae are used:
EtOAc ethyl acetate
DCM dichloromethane
DMF N,N-dimethylformamide
DMSO dimethyl sulfoxide
HCl hydrogen chloride
HPLC high-performance liquid chromatography
LCMS liquid chromatography/mass spectrometry
MeOH methanol
MeTHF 2-methyltetrahydrofuran
MHz MegaHertz
NaCl sodium chloride
$NaHCO_3$ sodium hydrogen carbonate
$Na_2SO_4$ sodium sulfate
NMP N-methylpyrrolidinone
$PdCl_2(dppf)$ [1,1'-bis(diphenylphosphino)ferrocene]dichloropalladium(II)
$Pd(PPh_3)_4$ tetrakis(triphenylphosphine)palladium(0)
$Pd(OAc)_2$ palladium(II) acetate
$Pd(t-Bu_3P)_2$ bis(tri-tert-butylphosphine)palladium(0)
$Pd(dba)_2$ bis(dibenzylideneacetone)palladium(0)
t-BuOK potassium tert-butoxide
TFA trifluoroacetic acid
THF tetrahydrofuran
THP tetrahydropyranyl
SEM 2-(trimethylsilyl)ethoxy]methyl
° C. degrees Celsius
min minute(s)
mL milliliter(s)
mmol millimole(s)
ppm parts per million In the text herein below:
the proton magnetic resonance spectra ($^1H$ NMR), as described below, are recorded at 400 MHz or 500 MHz in DMSO-$d_6$, using the DMSO-$d_6$ peak as reference. The chemical shifts δ are expressed in parts per million (ppm). The signals observed are expressed as follows: s=singlet; d=doublet; t=triplet; m=multiplet or br. s.=broad singlet;

the LCMS characteristics, as described below, successively indicated the high-performance liquid chromatography analytical method used and detailed below (A to E), the [M+H]$^+$ peak identified by mass spectrometry and the retention time (RT) of the compound, expressed in minutes.

Method A
Instrument: HPLC line of the type 1100 (Agilent) or Alliance (Waters); simple quadrupole mass spectrometer of the type MSD (Agilent) or ZQ (Waters)
Column: Symmetry C18 3.5 μm (2.1×50 mm) Waters
Solvent A: $H_2O$+0.005% TFA; Solvent B: $CH_3CN$+0.005% TFA
Flow rate: 0.4 mL/min
Gradient NB: 100/0 (t0 min) to 0/100 (t10 min) to 0/100 (t15 min)
Detection: UV 220 nm
Ionization: electrospray positive mode ESI+

Method B
Instrument: UPLC Acquity line (Waters); SQD mass spectrometer (Waters)
Column: BEH C18 (2.1×50 mm) 1.7 μm (Waters); column temp.: 55° C.
Solvent A: $H_2O$+0.02% HCOOH; Solvent B: $CH_3CN$+0.02% HCOOH
Flow rate: 1 mL/min
Gradient NB: 98/2 (t0 min) to 2/98 (t4 min) to 2/98 (t4.5 min)
Detection: UV 220 nm
Ionization: electrospray positive mode ESI+

Method C
Instrument: HPLC line of the type 1100 (Agilent) or Alliance (Waters); simple quadrupole mass spectrometer of the type MSD (Agilent) or ZQ (Waters)
Column: Luna C18(2)-HST Phenomenex (30×2 mm) 2.5 μm; column temp.: 50° C.
Solvent A: $H_2O$ +0.05% TFA; Solvent B: $CH_3CN$+0.035% TFA
Flow rate: 1 mL/min
Gradient NB: 100/0 (t0 min) to 0/100 (t2.5 min) to 0/100 (t3.5 min)
Detection: UV 220 nm
Ionization: electrospray positive mode ESI+

Method D
Instrument: Waters UPLC
Column: BEH C18 (2.1×50 mm) 1.7 μm
Solvent A: $H_2O$ +0.05% $HCO_2H$; Solvent B: $CH_3CN$+0.035% $HCO_2H$
Flow rate: 0.9 mL/min
Gradient NB: 95/5 (t0 min) to 5/95 (t1.1 min) to 5/95 (t1.7 min)
Detection: 220 nM
Ionization: electrospray positive mode ESI+

Method E
  Instrument: Waters UPLC
  Column: Waters XBridge C18 (4.6×50 mm) 2.5 µm
  Solvent A: $H_2O$ +0.1% $HCO_2H$; Solvent B: $CH_3CN$+ 0.08% $HCO_2H$
  Gradient NB: 97/3 (t0 min) to 40/60 (t3.5 min) to 2/98 (t4 min) to 2/98 (t5 min)
  Detection: 220 nM
  Ionization: electrospray positive mode ESI+

EXAMPLE 1

7-(2-chloropyridin-3-yl)-5-(2,2,2-trifluoroethyl)-1,5-dihydro-4H-pyrazolo[4,3-c][1,6]naphthyridin-4-one chloride (compound no.1)

Step 1.1. N-(2-chloro-5-iodopyridin-4-yl)-1-(tetrahydro-2H-pyran-2-yl)-1H-pyrazole-4-carboxamide 1-(Tetrahydro-2H-pyran-2-yl)-1H-pyrazole-4-carbonyl fluoride [CAS no. 848818-60-0] (8.99 g, 35 mmol) was added to a solution of 2-chloro-4-amino-5-iodopyridine [CAS no. 800402-12-4] (7.0 g, 35 mmol) and of t-BuOK (3.96 g, 35 mmol) in 180 ml of anhydrous THF stirred for 20 min at 0° C. and under nitrogen. The reaction mixture was stirred at ambient temperature for 3 h and then poured into a saturated aqueous solution of $NaHCO_3$ and extracted with EtOAc. The organic phase was washed with water and then with a saturated aqueous solution of NaCl, dried over $Na_2SO_4$, filtered and concentrated to dryness. After purification by silica flash chromatography (cyclohexane/EtOAc, gradient: from 90/10 to 50/50), 3.76 g of a white powder were obtained (yield: 25%).
  LCMS (method C): $[M+H]^+$=433.0, RT=2.17 min Step 1.2. N-(2-chloro-5-iodopyridin-4-yl)-N-(2,2,2-trifluoroethyl)-1-(tetrahydro-2H-pyran-2-yl)-1H-pyrazole-4-carboxamide t-BuOK (5.60 g, 50 mmol) was added portionwise at ambient temperature to a solution of N-(2-chloro-5-iodopyridin-4-yl)-1-(tetrahydro-2H-pyran-2-yl)-1H-pyrazole-4-carboxamide (18 g, 42 mmol) in 200 ml of anhydrous MeTHF under nitrogen. The reaction medium became yellow. After stirring the mixture at 60° C. for 30 min, 2,2,2-trifluoroethyltrifluoromethanesulfonate (7.2 ml, 50 mmol) was added. The reaction mixture was stirred at 60° C. for 2 h, poured into a saturated aqueous solution of $NaHCO_3$ and extracted with EtOAc. The organic phase was washed with water and then with a saturated aqueous solution of NaCl, dried over $Na_2SO_4$, filtered and concentrated to dryness. After purification by silica flash chromatography (cyclohexane/EtOAc, gradient: 80/20 to 40/60), 13.4 g of a white powder were obtained (yield: 62%).
  LCMS (method C): $[M+H]^+$=514.8, RT=2.31 min Step 1.3. 7-chloro-5-(2,2,2-trifluoroethyl)-1-(tetrahydro-2H-pyran-2-yl)-1,5-dihydro-4H-pyrazolo[4,3-c][1,6]naphthyridin-4-one Pd(PPh$_3$)$_4$ (2.83 g, 2 mmol) was added portionwise to a solution of N-(2-chloro-5-iodopyridin-4-yl)-N-(2,2,2-trifluoroethyl)-1-(tetrahydro-2H-pyran-2-yl)-1H-pyrazole-4-carboxamide (6.30 g, 12 mmol) and of potassium acetate (3.0 g, 31 mmol) in 150 ml of anhydrous DMF under nitrogen and which had been heated to 100° C. The reaction mixture was stirred at 100° C. for 2 h, cooled, concentrated to dryness. The residue was dissolved in EtOAc and the solution was washed with a saturated aqueous solution of $NaHCO_3$. The organic phase was washed with water and then with a saturated aqueous solution of NaCl, dried over $Na_2SO_4$, filtered and concentrated to dryness. After purification by silica flash chromatography (cyclohexane/acetone, gradient: 90/10 to 70/30), 2.70 g of a white powder were obtained (yield: 56%).
  LCMS (method C): $[M+H]^+$=387.0, RT=2.30 min Step 1.4. 7-(2-chloropyridin-3-yl)-1-(tetrahydro-2H-pyran-2-yl)-5-(2,2,2-trifluoroethyl)-1,5-dihydro-4H-pyrazolo[4,3-c][1,6]naphthyridin-4-one 7-Chloro-5-(2,2,2-trifluoroethyl)-1-(tetrahydro-2H-pyran-2-yl)-1,5-dihydro-4H-pyrazolo[4,3-c][1,6]naphthyridin-4-one (30 mg, 0.08 mmol), 2-chloro-3-pyridinylboronic acid (30 mg/0.16 mmol), Pd(PPh$_3$)$_4$ (20 mg, 0.02 mmol), potassium carbonate (0.60 g, 0.19 mmol), 0.8 ml of dioxane and 0.2 ml of water were successively introduced, under nitrogen, into a microwave reactor. The reactor was sealed and the reaction mixture was heated at 120° C. for 25 min in a microwave. The reaction medium was cooled, concentrated to dryness, taken up in EtOAc and poured into a saturated aqueous solution of $NaHCO_3$. The organic phase was washed with water and then with a saturated aqueous solution of NaCl, dried over $Na_2SO_4$, filtered and concentrated to dryness. After purification by silica flash chromatography (cyclohexane/DCM, gradient: 80/20 to 60/40), 10 mg of a white powder were obtained (yield: 24%).
  LCMS (method C): $[M+H]^+$=464.0, RT=2.28 min Step 1.5. 7-(2-chloropyridin-3-yl)-5-(2,2,2-trifluoroethyl)-1,5-dihydro-4H-pyrazolo[4,3-c][1,6]naphthyridin-4-one hydrochloride A 4M solution of anhydrous hydrogen chloride in dioxane (0.23 ml, 0.91 mmol) was added to a solution of 7-(2-chloropyridin-3-yl)-1-(tetrahydro-2H-pyran-2-yl)-5-(2,2,2-trifluoroethyl)-1,5-dihydro-4H-pyrazolo[4,3-c][1,6]naphthyridin-4-one (40 mg, 0.09 mmol) in 3 ml of DCM. After stirring at ambient temperature for 16 h, the precipitate formed was filtered off. The solid obtained was taken up in diisopropyl ether, filtered and dried under vacuum to give 20 mg of a white powder (hydrochloride, yield: 70%).
  LCMS (method B): $[M+H]^+$=380.0, RT=1.41 min
  $^1$H NMR [(CD$_3$)$_2$SO, 400 MHz]: 9.46 (1H, s); 8.61 (1H, s); 8.56 (1H, dd); 8.12 (1H, s); 8.08 (1H, dd); 7.63 (1H, dd); 5.42-5.30 (2H, q); 4.61 (1H, br s)

EXAMPLE 2

7-(2-chloropyridin-3-yl)-5-(2,2,2-trifluoroethyl)-1,5-dihydro-4H-pyrazolo[4,3-c][1,5]naphthyridin-4-one hydrochloride (compound no. 37)

Step 2.1. N-(2,5-dichloropyridin-3-yl)-1-(tetrahydro-2H-pyran-2-yl)-1H-pyrazole-4-carboxamide The product was obtained according to the procedure described in Step 1.1, using 4-amino-2,5-dichloropyridine [CAS no. 78607-32-6]. After purification by silica flash chromatography (cyclohexane/EtOAc, gradient: 80/20 to 50/50), a white powder was obtained (yield: 23%).
  LCMS (method B): $[M+H]^+$=341.0, RT=1.14 min

Step 2.2. N-(2,5-dichloropyridin-3-yl)-N-(2,2,2-trifluoroethyl)-1-(tetrahydro-2H-pyran-2-yl)-1H-pyrazole-4-carboxamide 2,2,2-Trifluoroethyltrifluoromethanesulfonate (1.47 ml, 10 mmol) was added to a solution of N-(2,5-dichloropyridin-3-yl)-1-(tetrahydro-2H-pyran-2-yl)-1H-pyrazole-4-carboxamide (2.90 g, 8.5 mmol) and of t-BuOK (1.14 g, 10 mmol) in 42 ml of anhydrous MeTHF stirred for 20 min at 60° C. and under nitrogen. The reaction mixture was heated at 60° C. for 2 h, cooled to ambient temperature, poured into water and extracted with EtOAc. The organic phase was washed with water and then with a saturated aqueous solution of NaCl, dried over $Na_2SO_4$, filtered and concentrated to dryness. After purification by silica flash chromatography (cyclohexane/EtOAc, gradient: from 100/0 to 80/20), the product was obtained in the form of a white powder (yield: 20%).

LCMS (method A): $[M+H]^+$=423.0; RT=8.42 min
$^1$H NMR [$(CD_3)_2SO$, 250 MHz]: 8.63 (1H, d); 8.51 (1H, d); 7.81 (1H, s); 7.05 (1H, s); 5.37 (1H, dd); 4.71-4.63 (2H, m); 3.81-3.56 (2H, m); 1.89-1.51 (6H, m).

Step 2.3. 7-chloro-5-(2,2,2-trifluoroethyl)-1-(tetrahydro-2H-pyran-2-yl)-1,5-dihydro-4H-pyrazolo[4,3-c][1,5]naphthyridin-4-one $Pd(PPh_3)_4$ (2.73 g, 2 mmol) was added to a solution of N-(2,5-dichloropyridin-3-yl)-N-(2,2,2-trifluoroethyl)-1-(tetrahydro-2H-pyran-2-yl)-1H-pyrazole-4-carboxamide (5 g, 12 mmol) and of potassium acetate (2.90 g, 30 mmol) in 150 ml of anhydrous DMF under a nitrogen stream and which had been heated to 100° C., and then the reaction mixture was stirred under nitrogen at 100° C. for 4 h. After cooling, the reaction medium was concentrated to dryness, diluted in EtOAc and poured into a saturated aqueous solution of $NaHCO_3$. The organic phase was washed with water and then with a saturated aqueous solution of NaCl, dried over $Na_2SO_4$, filtered and concentrated to dryness. After purification by silica flash chromatography (cyclohexane/EtOAc, gradient: 90/10 to 70/30), 3.25 g of a white powder were obtained (yield: 70%).

LCMS (method C): $[M+H]^+$=387.0, RT=2.45 min

Step 2.4. 7-(2-chloropyridin-3-yl)-1-(tetrahydro-2H-pyran-2-yl)-5-(2,2,2-trifluoroethyl)-1,5-dihydro-4H-pyrazolo[4,3-c][1,5]naphthyridin-4-one 7-Chloro-5-(2,2,2-trifluoroethyl)-1-(tetrahydro-2H-pyran-2-yl)-1,5-dihydro-4H-pyrazolo[4,3-c][1,5]naphthyridin-4-one (0.6 g, 1.56 mmol), 2-chloro-3-pyridinylboronic acid (0.29 g, 1.87 mmol), $Pd(t-Bu_3P)_2$ (0.16 g, 0.31 mmol), potassium carbonate (0.43 g, 3.12 mmol) and 15 ml of anhydrous DMF were successively introduced, under a nitrogen stream, into a microwave reactor. The reactor was sealed and the reaction mixture was heated at 120° C. for 15 min in a microwave. The reaction medium was cooled, concentrated to dryness, taken up in EtOAc and poured into a saturated aqueous solution of $NaHCO_3$. The organic phase was washed with water and then with a saturated aqueous solution of NaCl, dried over $Na_2SO_4$, filtered and concentrated to dryness. After purification by silica flash chromatography (cyclohexane/EtOAc, gradient: 90/10 to 75/35), 0.20 g of a white powder were obtained (yield: 28%).

LCMS (method C): $[M+H]^+$=464.0, RT=2.42 min

Step 2.5. 7-(2-chloropyridin-3-yl)-5-(2,2,2-trifluoroethyl)-1,5-dihydro-4H-pyrazolo[4,3-c][1,5]naphthyridin-4-one hydrochloride A 4M solution of anhydrous hydrogen chloride in dioxane (1.53 ml, 6.12 mmol) was added to a solution of 7-(2-chloropyridin-3-yl)-1-(tetrahydro-2H-pyran-2-yl)-5-(2,2,2-trifluoroethyl)-1,5-dihydro-4H-pyrazolo[4,3-c][1,5]naphthyridin-4-one (0.28 g, 0.61 mmol) in 10 ml of DCM. After stirring at ambient temperature for 1 h, the precipitate formed was filtered off. The solid obtained was taken up in diisopropyl ether, filtered and dried under vacuum to give 150mg of a white powder (hydrochloride, yield: 66%).

LCMS (method B): $[M+H]^+$=380.0, RT=6.69 min
$^1$H-NMR [$(CD_3)_2SO$, 400 MHz]: 11.18 (1H, s); 8.74 (1H, s); 8.56 (1H, dd); 8.46 (1H, s); 8.35 (1H, s); 8.06 (1H, dd); 7.66 (1H, dd); 5.33 (2H, q)

EXAMPLE 3

7-(pyridin-2-yl)-5-(2,2,2-trifluoroethyl)-1,5-dihydro-4H-pyrazolo[4,3-c][1,5]naphthyridin-4-one hydrochloride (compound no. 38)

Step 3.1. 7-(pyridin-2-yl)-1-(tetrahydro-2H-pyran-2-yl)-5-(2,2,2-trifluoroethyl)-1,5-dihydro-4H-pyrazolo[4,3-c][1,5]naphthyridin-4-one 7-Chloro-5-(2,2,2-trifluoroethyl)-1-(tetrahydro-2H-pyran-2-yl)-1,5-dihydro-4H-pyrazolo[4,3-c][1,5]naphthyridin-4-one (0.19 g, 0.5 mmol), 2-(tributylstannyl)pyridine (0.34 g, 0.7 mmol), $Pd(t-Bu_3P)_2$ (80 mg, 0.2 mmol) and 5 ml of anhydrous DMF were successively introduced, under an argon stream, into a microwave reactor. The reactor was sealed and the reaction mixture was heated at 120° C. for 10 min in a microwave, cooled, diluted with EtOAc and poured into water. The organic phase was washed with a saturated aqueous solution of NaCl, dried over $Na_2SO_4$, filtered and concentrated to dryness. After purification by silica flash chromatography (cyclohexane/EtOAc, gradient: 75/25 to 50/50), 66mg of a white powder were obtained (yield: 31%).

LCMS (method C): $[M+H]^+$=430.0, RT=2.37 min

Step 3.2. 7-(pyridin-2-yl)-1-(tetrahydro-2H-pyran-2-yl)-5-(2,2,2-trifluoroethyl)-1,5-dihydro-4H-pyrazolo[4,3-c][1,5]naphthyridin-4-one hydrochloride A 4M solution of hydrogen chloride in dioxane (0.4 ml, 1.5 mmol) was added to a solution of 7-(pyridin-2-yl)-1-(tetrahydro-2H-pyran-2-yl)-5-(2,2,2-trifluoroethyl)-1,5-dihydro-4H-pyrazolo[4,3-c][1,5]naphthyridin-4-one (0.06 g/0.15 mmol) in 5 ml of DCM. The reaction medium was stirred for 2 h at ambient temperature and filtered. The precipitate was washed with DCM and dried to give a white powder (hydrochloride; yield: 65%).

LCMS (method A): $[M+H]^+$=346.0, RT=6.57 min
$^1$H-NMR [$(CD_3)_2SO$, 400 MHz]: 9.32 (1H, s); 8.82 (1H, d); 8.76 (1H, s); 8.42 (1H, s); 8.33 (1H, d); 8.09 (1H, m); 7.55 (1H, m); 5.78 (2H, br s); 5.49-5.44 (2H, q).

EXAMPLE 4

3-[4-Oxo-5-(2,2,2-trifluoroethyl)-4,5-dihydro-1H-pyrazolo[4,3-c][1,5]naphthyridin-7-yl]-pyridine-2-carboxylic acid methyl ester hydrochloride (compound no. 41)

Step 4.1. 1,5-dihydro-1-(tetrahydro-2H-pyran-2-yl)-7-(4,4,5,5-tetramethyl-1,3,2-dioxaborolan-2-yl)-5-(2,2,2-trifluoroethyl)-4H-pyrazolo[4,3-c][1,5]naphthyridin-4-one Bis(pinacolato)diborane (13.8 g, 54 mmol) and potassium acetate (7.95 g, 34 mmol) were added to a solution of 7-chloro-5-(2,2,2-trifluoroethyl)-1-(tetrahydro-2H-pyran-2-yl)-1,5-dihydro-4H-pyrazolo[4,3-c][1,5]naphthyridin-4-one (5.25 g, 14 mmol) in 90 ml of anhydrous dioxane under nitrogen. After having stirred the mixture at 70° C. for 45 min, Pd(dba)$_2$ (1.56 g, 3 mmol) and tricyclohexylphosphine (1.90 g, 7 mmol) were added and then the reaction medium was heated at 70° C. for 2 h. The reaction medium was poured into water and extracted with EtOAc. The organic phase was washed with a saturated aqueous solution of NaCl, dried over Na$_2$SO$_4$, filtered and concentrated to dryness. The residue obtained was washed with petroleum ether in order to remove the excess bis(pinacolato)diborane and then eluted on 3-mercaptopropyl functionalised silica gel (Aldrich). The filtrate was concentrated to give 5.05 g of a brown powder (yield: 54%).

LCMS (method C): [M+H]$^+$=397.0, RT=1.97 min corresponds to the [4-oxo-1-(tetrahydro-2H-pyran-2-yl)-5-(2,2,2-trifluoroethyl)-4,5-dihydro-1H-pyrazolo[4,3-c][1,5]naphthyridin-7-yl]boronic acid which was obtained under the conditions of this analysis.

Step 4.2. methyl 3-[4-oxo-1-(tetrahydro-2H-pyran-2-yl)-5-(2,2,2-trifluoroethyl)-4,5-dihydro-1H-pyrazolo[4,3-c][1,5]naphthyridin-7-yl]pyridine-2-carboxylate and 3-[4-oxo-1-(tetrahydro-2H-pyran-2-yl)-5-(2,2,2-trifluoroethyl)-4,5-dihydro-1H-pyrazolo[4,3-c][1,5]naphthyridin-7-yl]pyridine-2-carboxylic acid 1,5-Dihydro-1-(tetrahydro-2H-pyran-2-yl)-7-(4,4,5,5-tetramethyl-1,3,2-dioxaborolan-2-yl)-5-(2,2,2-trifluoroethyl)-4H-pyrazolo[4,3-c][1,5]naphthyridin-4-one (0.5 g, 0.92 mmol), methyl 3-bromopyridine-2-carboxylate (0.24 g, 1.10 mmol), caesium carbonate (0.75 g, 2.30 mmol), PdCl$_2$(dppf) (0.15 g, 0.18 mmol), 9 ml of DMF and 2.3 ml of water were successively introduced, under a nitrogen stream, into a microwave reactor.

The reactor was sealed and the reaction mixture was heated at 120° C. for 10 min in a microwave. The reaction medium was concentrated to dryness and taken up in EtOAc and the solution was washed with water.

The organic phase was washed with a saturated aqueous solution of NaCl, dried over Na$_2$SO$_4$, filtered and concentrated to dryness. After purification by silica flash chromatography (cyclohexane/EtOAc, gradient: 70/30 to 40/60), 0.17 g of methyl 3-[4-oxo-1-(tetrahydro-2H-pyran-2-yl)-5-(2,2,2-trifluoroethyl)-4,5-dihydro-1H-pyrazolo[4,3-c][1,5]naphthyridin-7-yl]pyridine-2-carboxylate was obtained in the form of a brown powder (yield: 37%).

LCMS (method C): [M+H]$^+$=488.0, RT=2.22 min

The aqueous phase was acidified to pH=3 by adding 1M hydrochloric acid, and then extracted with EtOAc. The organic phase was washed with water and then with a saturated aqueous solution of NaCl, dried over Na$_2$SO$_4$, filtered and concentrated to dryness to give 0.16 g of 3-[4-oxo-1-(tetrahydro-2H-pyran-2-yl)-5-(2,2,2-trifluoroethyl)-4,5-dihydro-1H-pyrazolo[4,3-c][1,5]naphthyridin-7-yl]pyridine-2-carboxylic acid in the form of a beige powder (yield: 36%).

LCMS (method C): [M+H]$^+$=474.0, RT=1.94 min

Step 4.3. methyl 3-[4-oxo-5-(2,2,2-trifluoroethyl)-4,5-dihydro-1H-pyrazolo[4,3-c][1,5]naphthyridin-7-yl]pyridine-2-carboxylate hydrochloride The product was obtained according to the procedure described in Step 1.5., using methyl 3-[4-oxo-1-(tetrahydro-2H-pyran-2-yl)-5-(2,2,2-trifluoroethyl)-4,5-dihydro-1H-pyrazolo[4,3-c][1,5]naphthyridin-7-yl]pyridine-2-carboxylate (0.17 g, 0.35 mmol); 0.10 g of a white powder was obtained (hydrochloride, yield: 70%).

LCMS (method B): [M+H]$^+$=404.1, RT=1.26 min
$^1$H-NMR [(CD$_3$)$_2$SO, 400 MHz]: 8.75 (1H, dd); 8.58 (1H, d); 8.42 (1H, s); 8.31 (1H, d); 8.07 (1H, dd); 7.80 (1H, dd); 5.31 (2H, q); 3.69 (3H, s)

EXAMPLE 5

7-[2-(pyrrolidin-1-yl)pyridin-3-yl]-5-(2,2,2-trifluoroethyl)-1,5-dihydro-4H-pyrazolo[4,3-c][1,6]naphthyridin-4-one hydrochloride (compound no. 33)

Step 5.1. 7-(2-fluoropyridin-3-yl)-1-(tetrahydro-2H-pyran-2-yl)-5-(2,2,2-trifluoroethyl)-1,5-dihydro-4H-pyrazolo[4,3-c][1,6]naphthyridin-4-one 7-Chloro-5-(2,2,2-trifluoroethyl)-1-(tetrahydro-2H-pyran-2-yl)-1,5-dihydro-4H-pyrazolo[4,3-c][1,6]naphthyridin-4-one (1.5 g, 3.88 mmol), 2-fluoro-3-pyridinylboronic acid (1.09 g, 7.76 mmol), Pd(PPh$_3$)$_4$ (0.90 g, 0.78 mmol), caesium carbonate (3.16 g, 9.70 mmol), 40 ml of dioxane and 10 ml of water were successively introduced, under a nitrogen stream, into a microwave reactor. The reactor was sealed and the reaction mixture was heated at 120° C. for 10 min in a microwave. The reaction medium was concentrated to dryness, taken up in EtOAc and poured into a saturated aqueous solution of NaHCO$_3$. The organic phase was washed with water and then with a saturated aqueous solution of NaCl, dried over Na$_2$SO$_4$, filtered and concentrated to dryness. After purification by silica flash chromatography (DCM/acetone, gradient: 100/0 to 96/4), 1.3 g of a white powder were obtained (yield: 75%).

LCMS (method C): [M+H]$^+$=448.0, RT=2.32 min

Step 5.2. 7-[2-(pyrrolidin-1-yl)pyridin-3-yl]-1-(tetrahydro-2H-pyran-2-yl)-5-(2,2,2-trifluoroethyl)-1,5-dihydro-4H-pyrazolo[4,3-c][1,6]naphthyridin-4-one 7-(2-Fluoropyridin-3-yl)-1-(tetrahydro-2H-pyran-2-yl)-5-(2,2,2-trifluoroethyl)-1,5-dihydro-4H-pyrazolo[4,3-c][1,6]naphthyridin-4-one (0.20 g, 0.44 mmol) and pyrrolidine (3.69 ml, 43.6 mmol) were successively introduced into a microwave reactor. The reactor was sealed and the reaction mixture was heated at 130° C. for 40 min in a microwave, cooled and concentrated to dryness. After purification of the residue by flash chromatography on an amine phase (RediSep Rf Gold® Amine) (cyclohexane/DCM, gradient: 60/40 to 40/60), 0.21 g of a beige powder were obtained (yield: 98%).

LCMS (method C): [M+H]$^+$=499.1, RT=1.98 min

Step 5.3. 7-[2-(pyrrolidin-1-yl)pyridin-3-yl]-5-(2,2,2-trifluoroethyl)-1,5-dihydro-4H-pyrazolo[4,3-c][1,6]naphthyridin-4-one hydrochloride The product was obtained according to the procedure described in Step 1.5, using 7-[2-(pyrrolidin-1-yl)pyridin-3-yl]-1-(tetrahydro-2H-pyran-2-yl)-5-(2,2,2-trifluoroethyl)-1,5-dihydro-4H-pyrazolo[4,3-c][1,6]naphthyridin-4-one, in the form of a beige powder (2 hydrochloride, yield: 85%).
LCMS (method B): [M+H]$^+$=415.2, RT=0.96 min $^1$H-NMR [(CD$_3$)$_2$SO, 400 MHz]: 13-14 (1H, br s); 9.45 (1H, s); 8.63 (1H, s); 8.15 (1H, dd); 8.03 (1H, d); 7.99 (1H, s); 7.10 (1H, t); 5.28 (2H, q); 3.21 (4H, s); 1.83 (4H, s)

The table that follows illustrates the chemical structures and the physical properties of a number of compounds according to the invention. In this table, in the "salt" column "/" represents a compound in free base form, whereas "HCl" represents a compound in the form of the hydrochloride salt and "TFA" represents a compound in the form of the trifluoroacetic acid salt.

TABLE

| Compound No. | X | Y | R1 | R2 | salt | chemical route | [M + H]+ | RT (Min) | LC/MS Method |
|---|---|---|---|---|---|---|---|---|---|
| 1 (Example 1) | N | CH | CH2CF3 | 2-chloropyridin-3-yl (with methyl linker) | HCl | A | 380.0 | 1.41 | B |
| 2 | N | CH | CH2CF3 | 2-Pyridyl | HCl | A | 346.0 | 6.43 | A |
| 3 | N | CH | CH2CF3 | 2-(4-methylpiperazin-1-yl)pyridin-4-yl (with methyl linker) | HCl | A | 444.0 | 5.03 | A |
| 4 | N | CH | CH2CF3 | 4-fluorophenyl (with methyl linker) | / | A | 363.1 | 1.81 | D |
| 5 | N | CH | CH2CF3 | 2-methylphenyl (with methyl linker) | / | A | 359.1 | 1.78 | D |
| 6 | N | CH | CH2CF3 | 2-(trifluoromethyl)phenyl (with methyl linker) | / | A | 413.1 | 1.82 | D |
| 7 | N | CH | CH2CF3 | 2-fluorophenyl (with methyl linker) | / | A | 363.1 | 1.77 | D |

TABLE-continued

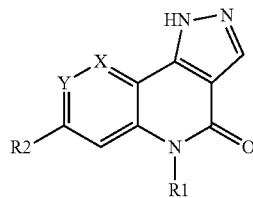

| Compound No. | X | Y | R1 | R2 | salt | chemical route | [M + H]+ | RT (Min) | LC/MS Method |
|---|---|---|---|---|---|---|---|---|---|
| 8 | N | CH | CH2CF3 | 4-Pyridyl | TFA | A | 346.1 | 1.34 | D |
| 9 | N | CH | CH2CF3 | 8-quinolinyl | / | A | 396.1 | 1.53 | D |
| 10 | N | CH | CH2CF3 | 2-(trifluoromethoxy)phenyl | / | A | 429.1 | 1.87 | D |
| 11 | N | CH | CH2CF3 | 2-carbamoylphenyl | / | A | 388.1 | 3.76 | E |
| 12 | N | CH | CH2CF3 | 4-morpholinophenyl | TFA | A | 430.2 | 1.70 | D |
| 13 | N | CH | CH2CF3 | 6-amino-3-pyridyl | TFA | A | 361.1 | 2.31 | E |
| 14 | N | CH | CH2CF3 | 2-fluoro-4-methoxyphenyl | / | A | 393.1 | 1.80 | D |
| 15 | N | CH | CH2CF3 | 4-(phenylcarbamoyl)phenyl | / | A | 464.1 | 1.82 | D |
| 16 | N | CH | CH2CF3 | 4-fluoro-3-(methylcarbamoyl)phenyl | / | A | 420.1 | 1.60 | D |

TABLE-continued

| Compound No. | X | Y | R1 | R2 | salt | chemical route | [M + H]+ | RT (Min) | LC/MS Method |
|---|---|---|---|---|---|---|---|---|---|
| 17 | N | CH | CH2CF3 | 2-(morpholinomethyl)phenyl | TFA | A | 444.2 | 1.42 | D |
| 18 | N | CH | CH2CF3 | 2-(ethoxymethyl)phenyl | / | A | 403.1 | 1.81 | D |
| 19 | N | CH | CH2CF3 | 2-(N-methylsulfamoyl)phenyl | / | A | 438.1 | 1.70 | D |
| 20 | N | CH | CH2CF3 | 3-chloro-2-hydroxyphenyl | / | A | 395.1 | 4.56 | E |
| 21 | N | CH | CH2CF3 | 2-(2-(pyrrolidin-1-yl)ethoxy)phenyl | TFA | A | 458.1 | 1.43 | D |
| 22 | N | CH | CH2CF3 | 2-(methylsulfonamido)phenyl | / | A | 438.1 | 1.75 | D |

TABLE-continued

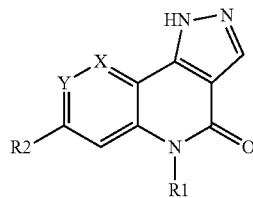

| Compound No. | X | Y | R1 | R2 | salt | chemical route | [M + H]+ | RT (Min) | LC/MS Method |
|---|---|---|---|---|---|---|---|---|---|
| 23 | N | CH | CH2CF3 | 3-(1H-pyrazol-1-yl)phenyl | / | A | 411.1 | 1.78 | D |
| 24 | N | CH | CH2CF3 | 6-chloro-2-methylpyridin-3-yl | / | A | 394.1 | 1.72 | D |
| 25 | N | CH | CH2CF3 | 4-(N-isopropylsulfamoyl)phenyl | / | A | 466.1 | 1.74 | D |
| 26 | N | CH | CH2CF3 | 2-isopropoxypyridin-4-yl | TFA | A | 404.1 | 1.88 | D |
| 27 | N | CH | CH2CF3 | 5-methoxypyridin-3-yl | TFA | A | 376.1 | 3.04 | E |
| 28 | N | CH | CH2CF3 | 2-ethoxypyridin-3-yl | TFA | A | 390.1 | 1.80 | D |
| 29 | N | CH | CH2CF3 | 2-(N,N-dimethylsulfamoyl)phenyl | / | A | 452.1 | 1.67 | D |
| 30 | N | CH | CH2CF3 | 4-(N-ethylsulfamoyl)phenyl | / | A | 452.1 | 1.69 | D |

TABLE-continued

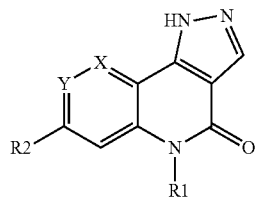

| Compound No. | X | Y | R1 | R2 | salt | chemical route | [M + H]+ | RT (Min) | LC/MS Method |
|---|---|---|---|---|---|---|---|---|---|
| 31 | N | CH | CH2CF3 | (4-methylpiperazinyl-pyridinyl) | TFA | A | 444.2 | 1.29 | D |
| 32 | N | CH | CH2CF3 | (morpholino-phenyl) | TFA | A | 430.2 | 1.66 | D |
| 33 (Example 5) | N | CH | CH2CF3 | (pyrrolidinyl-pyridinyl) | HCl | C | 415.0 | 0.96 | B |
| 34 | N | CH | CH2CF3 | (homopiperazinyl-pyridinyl) | HCl | C | 444.0 | 0.97 | B |
| 35 | N | CH | CH2CF3 | (N-ethyl-N-methylamino-pyridinyl) | HCl | C | 403.2 | 1.14 | B |
| 36 | N | CH | CH2CF3 | (2-fluoropyridin-3-yl) | / | A | 364.1 | 1.45 | B |
| 37 (Example 2) | CH | N | CH2CF3 | (2-chloropyridin-3-yl) | / | A | 380.0 | 6.69 | A |

TABLE-continued

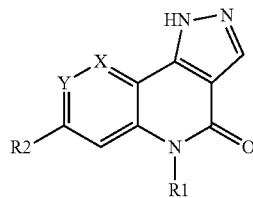

| Compound No. | X | Y | R1 | R2 | salt | chemical route | [M + H]+ | RT (Min) | LC/MS Method |
|---|---|---|---|---|---|---|---|---|---|
| 38 (Example 3) | CH | N | CH2CF3 | 2-Pyridyl | HCl | A | 346.0 | 6.57 | A |
| 39 | CH | N | CH2CF3 | 4-Pyridyl | HCl | A | 346.0 | 8.50 | A |
| 40 | CH | N | CH2CF3 | ![4-(4-methylpiperazin-1-yl)pyridin-2-yl] | HCl | A | 444.0 | 5.01 | A |
| 41 (Example 4) | CH | N | CH2CF3 | ![methyl 3-pyridine-2-carboxylate] | / | B | 404.1 | 1.26 | B |
| 42 | CH | N | CH2CF3 | ![6-aminopyridin-2-yl] | TFA | B | 361.1 | 2.42 | E |
| 43 | CH | N | CH2CF3 | ![2-(dimethylamino)phenyl] | TFA | B | 388.1 | 1.89 | D |
| 44 | CH | N | CH2CF3 | ![3-(trifluoromethyl)pyridin-2-yl] | TFA | B | 414.1 | 1.71 | D |
| 45 | CH | N | CH2CF3 | ![5-(trifluoromethyl)pyridin-2-yl] | TFA | B | 414.1 | 1.86 | D |
| 46 | CH | N | CH2CF3 | ![2-cyanopyridin-3-yl] | / | B | 371.1 | 1.57 | D |

TABLE-continued

| Compound No. | X | Y | R1 | R2 | salt | chemical route | [M + H]+ | RT (Min) | LC/MS Method |
|---|---|---|---|---|---|---|---|---|---|
| 47 | CH | N | CH2CF3 | (2-((cyclopropylamino)methyl)phenyl) | TFA | B | 414.2 | 1.36 | D |
| 48 | CH | N | CH2CF3 | (6-cyclopentylpyrimidin-5-yl) | TFA | B | 415.2 | 1.78 | D |
| 49 | CH | N | CH2CF3 | (5-chloro-2-methoxypyridin-3-yl) | TFA | B | 410.1 | 1.87 | D |
| 50 | CH | N | CH2CF3 | (2-((methylamino)methyl)pyridin-3-yl) | TFA | B | 389.1 | 1.11 | D |
| 51 | CH | N | CH2CF3 | (6-isopropylpyrimidin-5-yl) | TFA | B | 389.1 | 1.67 | D |
| 52 | CH | N | CH2CF3 | (5-chloropyridin-2-yl) | TFA | B | 380.1 | 4.03 | E |
| 53 | CH | N | CH2CF3 | (3-chloropyridin-2-yl) | TFA | B | 380.1 | 1.68 | D |

TABLE-continued
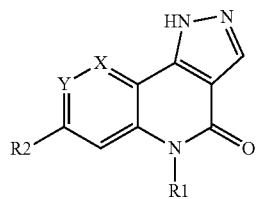
| Compound No. | X | Y | R1 | R2 | salt | chemical route | [M + H]+ | RT (Min) | LC/MS Method |
|---|---|---|---|---|---|---|---|---|---|
| 54 | CH | N | CH2CF3 | 4-methyl-2-amino-pyrimidin-6-yl | TFA | B | 376.1 | 2.61 | E |
| 55 | CH | N | CH2CF3 | 2-aminophenyl | TFA | B | 360.1 | 1.69 | D |
| 56 | CH | N | CH2CF3 | 4-trifluoromethylphenyl | / | B | 413.1 | 1.94 | D |
| 57 | CH | N | CH2CF3 | 2-(2-hydroxyethyl)phenyl | / | B | 389.1 | 1.67 | D |
| 58 | CH | N | CH2CF3 | 3-cyanopyridin-2-yl | TFA | B | 371.1 | 3.25 | E |
| 59 | CH | N | CH2CF3 | 6-methylpyrimidin-4-yl | TFA | B | 361.1 | 3.11 | E |
| 60 | CH | N | CH2CF3 | 6-trifluoromethylpyridin-3-yl | / | B | 414.1 | 1.81 | D |
| 61 | CH | N | CH2CF3 | 3-aminopyridin-4-yl | TFA | B | 361.1 | 1.09 | D |

TABLE-continued
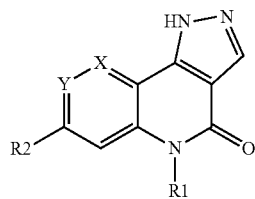
| Compound No. | X | Y | R1 | R2 | salt | chemical route | [M + H]+ | RT (Min) | LC/MS Method |
|---|---|---|---|---|---|---|---|---|---|
| 62 | CH | N | CH2CF3 | ![phenyl-NHC(O)propyl] | / | B | 430.2 | 1.68 | D |
| 63 | CH | N | CH2CF3 | ![pyrimidinyl-cyclohexyl] | TFA | B | 429.2 | 1.83 | D |
| 64 | CH | N | CH2CF3 | ![phenyl-NHC(O)isopropyl] | / | B | 430.2 | 1.68 | D |
| 65 | CH | N | CH2CF3 | ![2-acetylphenyl] | / | B | 387.1 | 3.72 | E |
| 66 | CH | N | CH2CF3 | ![4-(cyclopropylcarbonyl)phenyl] | / | B | 449.1 | 1.83 | D |
| 67 | CH | N | CH2CF3 | 3-Pyridyl | TFA | B | 346.1 | 1.43 | D |
| 68 | CH | N | CH2CF3 | ![3-X-pyridine-2-carboxylic acid] | / | B | 390.2 | 0.89 | A |

The compounds according to the invention underwent biochemical studies in order to determine their capacity to inhibit the enzyme methionine-aminopeptidase2 (enzymatic test on isolated enzyme).

MetAP2 Enzymatic Screening Test

For the enzymatic test, human MetAP2 protein was obtained from a culture supernatant of insect cells (sf9) infected with MetAP2 recombinant baculovirus.

Before performing the experiment, dialysis of the MetAP2 supernatant was performed over 24 hours at 4° C. in a buffer (10 mM Hepes, 100 mM KCl, 10% glycerol, pH 7.4) in the presence of EDTA (1 mM) over the first 12 hours.

The dialysis supernatant was recovered and manganese, used as cofactor, was added to a final concentration of 300 µM.

The enzymatic test is a two steps procedure.

In a first step, it consists in placing in contact the compound according to the invention, the dialysed MetAP2 protein and the substrate (Met-Pro-Arg-pNa peptide synthesized by Neosystem), the N-terminal methionine of which can be cleaved with MetAP2, and which bears at the C-terminal end a para-nitroaniline (pNa) chromophore, which can itself be released by another peptidase only when the N-terminal methionine has been cleaved beforehand.

Consequently, the second step consists in reacting the peptides cleaved in the preceding step with a second peptidase in order to release the chromophore. The peptidase used in this second step is cathepsin, which comes from the TagZyme "DAPase" kit (Quiagen, 34366).

The MetAP2 activity is proportional to the amount of para-nitroaniline released, which is measured by absorbance at 405 nm.

The inhibitory activity with respect to MetAP2 is given by the concentration which inhibits 50% of activity of MetAP2.

The $IC_{50}$ values for the compounds of the invention were generally less than 1.1 µM, more particularly between 1 and 550 nM and even more particularly between 1 and 100 nM, as indicated in the table below:

| Compound No. | hMETAP2 $IC_{50}$ (nM) |
|---|---|
| 1 | 11 |
| 2 | 64 |
| 3 | 24 |
| 4 | 234 |
| 5 | 3 |
| 6 | 20 |
| 7 | 45 |
| 8 | 60 |
| 9 | 38 |
| 10 | 72 |
| 11 | 1020 |
| 12 | 75 |
| 13 | 102 |
| 14 | 19 |
| 15 | 165 |
| 16 | 20 |
| 17 | 75 |
| 18 | 49 |
| 19 | 4 |
| 20 | 61 |
| 21 | 162 |
| 22 | 8 |
| 23 | 41 |
| 24 | 54 |
| 25 | 62 |
| 26 | 109 |
| 27 | 199 |
| 28 | 146 |
| 29 | 82 |
| 30 | 42 |
| 31 | 5 |
| 32 | 187 |
| 33 | 6 |
| 34 | 12 |
| 35 | 38 |
| 36 | 31 |
| 37 | 20 |
| 38 | 28 |
| 39 | 37 |
| 40 | 11 |
| 41 | 34 |
| 42 | 26 |
| 43 | 196 |
| 44 | 28 |
| 45 | 226 |
| 46 | 40 |
| 47 | 21 |
| 48 | 62 |
| 49 | 1090 |
| 50 | 459 |
| 51 | 379 |
| 52 | 38 |
| 53 | 13 |
| 54 | 45 |
| 55 | 37 |
| 56 | 339 |
| 57 | 6 |
| 58 | 61 |
| 59 | 58 |
| 60 | 188 |
| 61 | 37 |
| 62 | 46 |
| 63 | 118 |
| 64 | 201 |
| 65 | 41 |
| 66 | 20 |
| 67 | 52 |
| 68 | 727 |

In order to determine the selectivity of the compounds of the invention towards the protein MetAP1, an enzymatic test on the isolated enzyme was performed. The MetAP1 recombinant protein was produced in Escherichia coli.

The MetAP1 enzymatic test is based on the same principle as the MetAP2 test.

The MetAP1 activity is proportional to the amount of para-nitroaniline released, which is measured by absorbance at 405 nm.

The compounds of the invention showed no activity at 10 µM.

It thus appears that the compounds according to the invention have selective inhibitory activity on MetAP2.

The compounds according to the invention may thus be used as inhibitors of MetAP2.

The compounds according to the invention may thus be used for the preparation of medicaments, especially medicaments which are inhibitors of MetAP2.

Thus, according to another of its aspects, a subject of the invention is medicaments that comprise a compound of formula (I), or an addition salt thereof with a pharmaceutically acceptable acid.

The compounds according to the invention may be thus used in the treatment or prevention of pathologies involving MetAP2 inhibitors.

Thus, the compounds according to the invention may be used in the treatment or prevention of pulmonary and hepatic fibrosis.

The compounds according to the invention may also be used in the treatment or prevention of pathologies involving a reactivation of angiogenesis, such as diabetic retinopathy, age-related macular degeneration (ARMD) and psoriasis.

The compounds according to the invention may also be used in the treatment or prevention of any carcinoma having a substantial degree of vascularization, such as lung, breast, prostate, oesophageal, pancreatic, liver, colon or kidney carcinomas or carcinomas that induce metastases, such as colon, breast, liver and stomach carcinomas, and melanomas. These compounds may be used in monotherapy or combination with radiotherapy or chemotherapy.

The compounds according to the invention may also be used in antitumour treatment, alone or in combination with chemotherapy or solid tumours, such as pancreatic, breast, prostate, colon or kidney tumours, neuroblastomas and Kaposi's sarcoma.

The compounds according to the invention may also be used in the treatment or prevention of hepatocarcinomas, cholangiocarcinoma and also malignant mesothelioma, pancreatic cancer, haemoangioma, endometriosis, arthritis and in particular rheumatoid arthritis, autoimmune diseases, obesity and microsporidiosis.

According to another of its aspects, the present invention relates to pharmaceutical compositions comprising, as active principle, a compound according to the invention.

These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, for the prevention or treatment of the above disorders or diseases.

The appropriate unit administration forms include oral-route forms such as tablets, soft or hard gel capsules, powders, granules and oral solutions or suspensions, sublingual, buccal, intratracheal, intraocular, intranasal or inhalation administration forms, topical, parenteral such as transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---:|
| Compound according to the invention | 50.0 mg |
| Mannitol | 223.75 mg |
| Croscaramellose sodium | 6.0 mg |
| Corn starch | 15.0 mg |
| Hydroxypropylmethylcellulose | 2.25 mg |
| Magnesium stearate | 3.0 mg |

The dose of active principle administered per day may range from 0.01 to 100 mg/kg and preferentially 0.02 to 50 mg/kg, in one or more dosage intakes. In general, the daily dose of the compound of the invention will be the lowest effective dose of the compound that is capable of producing a therapeutic effect.

There may be particular cases in which higher or lower dosages are appropriate; such dosages do not depart from the scope of the invention. According to the usual practice, the dosage that is appropriate for each patient is determined by the doctor according to the mode of administration and the weight and response of the said patient.

According to another of its aspects, the present invention also relates to a method for treating the pathologies indicated above, which comprises the administration, to a patient, of an effective dose of a compound according to the invention, or a pharmaceutically acceptable salt thereof.

The invention claimed is:
1. A compound of Formula (I)

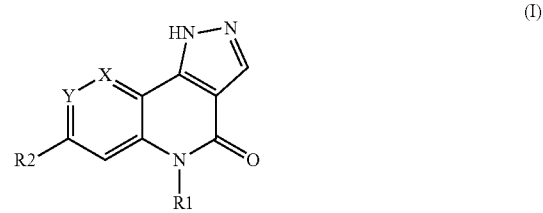

wherein:
X is CH or a nitrogen atom;
Y is CH or a nitrogen atom,
  wherein X or Y is a nitrogen atom;
$R_1$ is a $(C_1-C_4)$alkyl, wherein the $(C_1-C_4)$alkyl is a non-substituted or substituted with one or more halogen atoms;
$R_2$ is an aryl or a heteroaryl group, wherein the aryl or heteroaryl group is non substituted or substituted with one or more substituents independently selected from the group consisting of:
  a halogen atom,
  a $(C_1-C_4)$alkyl group, wherein the alkyl group is non-substituted or substituted with one or more substituents independently selected from the group consisting of a halogen atom, a heterocyclyl, $(C_1-C_4)$alkoxy, a hydroxy group, and $NHR_3$,
  $O-R_4$,
  $(CO)NR_5R_{5'}$,
  a heterocyclyl group, wherein the heterocyclyl group is non substituted or substituted with one or more $(C_1-C_4)$alkyl group,
  a cycloalkyl group,
  a cyano group,
  $NR_6R_{6'}$,
  $SO_2NR_6R_{6'}$,
  $NHSO_2R_7$,
  $NH(CO)R_7$,
  $(CO)R_8$, and
  a heteroaryl group;
$R_3$ is a $(C_1-C_4)$alkyl or a cycloalkyl group;
$R_4$ is a hydrogen atom or a $(C_1-C_4)$alkyl group, wherein the alkyl group is non-substituted or substituted with one or more halogen atom or heterocyclyl group;
$R_5$ and $R_{5'}$ are independently a hydrogen atom, a $(C_1-C_4)$alkyl or aryl group;
$R_6$ and $R_{6'}$ are independently a hydrogen atom or a $(C_1-C_4)$alkyl group;
$R_7$ is a $(C_1-C_4)$alkyl group; and
$R_8$ is selected from the group consisting of a $(C_1-C_4)$alkyl, $(C_1-C_4)$alkoxy, cycloalkyl and a hydroxy group;

or an enantiomers, diastereoisomers, or tautomers thereof, or a base or addition salt with an acid of any of the foregoing.

2. The compound according to claim 1, wherein X is a nitrogen atom and Y is CH, or an enantiomer, diastereoisomer, or tautomer thereof, or a base or addition salt with an acid of any of the foregoing.

3. The compound according to claim 1, wherein X is CH and Y is a nitrogen atom, or an enantiomer, diastereoisomer, or tautomer thereof, or a base or addition salt with an acid of any of the foregoing.

4. The compound according to claim 1, wherein $R_1$ is a $(C_1-C_4)$alkyl group, wherein the $(C_1-C_4)$alkyl group is non-substituted or substituted with one or more fluorine atoms, or an enantiomer, diastereoisomer, or tautomer thereof, or a base or addition salt with an acid of any of the foregoing.

5. The compound according to claim 4, wherein $R_1$ is a trifluoroethyl group, or an enantiomer, diastereoisomer, or tautomer thereof, or a base or addition salt with an acid of any of the foregoing.

6. The compound according to claim 1, wherein $R_2$ is an aryl group, wherein the aryl group is non-substituted or substituted with one or more substituents independently selected from the group consisting of:
   a halogen atom,
   a $(C_1-C_4)$alkyl group, wherein the alkyl group is non-substituted or substituted with one or more substituents independently selected from the group consisting of a halogen atom, a heterocyclyl, $(C_1-C_4)$alkoxy, hydroxy group, and $NHR_3$,
   a hydroxy group,
   O—$R_4$,
   (CO)$NHR_5$,
   a heterocyclyl group, wherein the heterocyclyl group is non-substituted or substituted with a $(C_1-C_4)$alkyl group,
   $NR_6R_{6'}$,
   $SO_2NR_6 R_{6'}$,
   $NHSO_2R_7$,
   NH(CO)$R_7$,
   (CO)$R_8$, and
   a heteroaryl group;
or an enantiomer, diastereoisomer, or tautomer thereof, or a base or addition salt with an acid of any of the foregoing.

7. The compound according to claim 6, wherein $R_2$ is a phenyl group, or an enantiomer, diastereoisomer, or tautomer thereof, or a base or addition salt with an acid of any of the foregoing.

8. The compound according to claim 1, wherein $R_2$ is a heteroaryl group, wherein the heteroaryl group is non-substituted or substituted with one or more substituents independently selected from the group consisting of:
   a halogen atom,
   a $(C_1-C_4)$alkyl group, wherein the alkyl group is non-substituted or substituted with one or more substituents independently selected from the group consisting of a halogen atom, a heterocyclyl, $(C_1-C_4)$alkoxy, hydroxy group, and $NHR_3$,
   O—$R_4$,
   a heterocyclyl group, wherein the heterocyclyl group is non-substituted or substituted with a $(C_1-C_4)$alkyl group,
   a cycloalkyl group,
   a cyano group,
   $NR_6R_{6'}$, and
   (CO)$R_8$;

or an enantiomer, diastereoisomer, or tautomer thereof, or a base or addition salt with an acid of any of the foregoing.

9. The compound according to claim 8, wherein $R_2$ is an heteroaryl group comprising 1 or 2 nitrogen atoms, or an enantiomer, diastereoisomer, or tautomer thereof, or a base or addition salt with an acid of any of the foregoing.

10. The compound according to claim 1, wherein $R_2$ is a pyridine, a pyrimidine or a quinoline group, or an enantiomer, diastereoisomer, or tautomer thereof, or a base or addition salt with an acid of any of the foregoing.

11. A compound selected from the group consisting of:
   7-(2-Chloro-pyridin-3-yl)-5-(2,2,2-trifluoro-ethyl)-1,5-dihydro-pyrazolo[4,3-c][1,6]naphthyridin-4-one;
   7-Pyridin-2-yl-5-(2,2,2-trifluoro-ethyl)-1,5-dihydro-pyrazolo[4,3-c][1,6]naphthyridin-4-one;
   7-[2-(4-Methyl-piperazin-1-yl)-pyridin-4-yl]-5-(2,2,2-trifluoro-ethyl)-1,5-dihydro-pyrazolo[4,3-c][1,6]naphthyridin-4-one;
   7-(4-Fluoro-phenyl)-5-(2,2,2-trifluoro-ethyl)-1,5-dihydro-pyrazolo[4,3-c][1,6]naphthyridin-4-one;
   7-o-Tolyl-5-(2,2,2-trifluoro-ethyl)-1,5-dihydro-pyrazolo[4,3-c][1,6]naphthyridin-4-one;
   5-(2,2,2-Trifluoro-ethyl)-7-(2-trifluoromethyl-phenyl)-1,5-dihydro-pyrazolo[4,3-c][1,6]naphthyridin-4-one;
   7-(2-Fluoro-phenyl)-5-(2,2,2-trifluoro-ethyl)-1,5-dihydro-pyrazolo[4,3-c][1,6]naphthyridin-4-one;
   7-Pyridin-4-yl-5-(2,2,2-trifluoro-ethyl)-1,5-dihydro-pyrazolo[4,3-c][1,6]naphthyridin-4-one;
   7-Quinolin-8-yl-5-(2,2,2-trifluoro-ethyl)-1,5-dihydro-pyrazolo[4,3-c][1,6]naphthyridin-4-one;
   5-(2,2,2-Trifluoro-ethyl)-7-(2-trifluoromethoxy-phenyl)-1,5-dihydro-pyrazolo[4,3-c][1,6]naphthyridin-4-one;
   2-[4-Oxo-5-(2,2,2-trifluoro-ethyl)-4,5-dihydro-1H-pyrazolo[4,3-c][1,6]naphthyridin-7-yl]-benzamide;
   7-(4-Morpholin-4-yl-phenyl)-5-(2,2,2-trifluoro-ethyl)-1,5-dihydro-pyrazolo[4,3-c][1,6]naphthyridin-4-one;
   7-(6-Amino-pyridin-3-yl)-5-(2,2,2-trifluoro-ethyl)-1,5-dihydro-pyrazolo[4,3-c][1,6]naphthyridin-4-one;
   7-(2-Fluoro-4-methoxy-phenyl)-5-(2,2,2-trifluoro-ethyl)-1,5-dihydro-pyrazolo[4,3-c][1,6]naphthyridin-4-one;
   4-[4Oxo-5-(2,2,2-trifluoro-ethyl)-4,5-dihydro-1H-pyrazolo[4,3-c][1,6]naphthyridin-7-yl]-N-phenyl-benzamide;
   2-Fluoro-N-methyl-5-[4-oxo-5-(2,2,2-trifluoro-ethyl)-4,5-dihydro-1H-pyrazolo[4,3-c][1,6]naphthyridin-7-yl]-benzamide;
   7-(2-Morpholin-4-ylmethyl-phenyl)-5-(2,2,2-trifluoro-ethyl)-1,5-dihydro-pyrazolo[4,3-c][1,6]naphthyridin-4-one;
   7-(2-Ethoxymethyl-phenyl)-5-(2,2,2-trifluoro-ethyl)-1,5-dihydro-pyrazolo[4,3-c] [1,6]naphthyridin-4-one;
   N-Methyl-2-[4-oxo-5-(2,2,2-trifluoro-ethyl)-4,5-dihydro-1H-pyrazolo[4,3-c][1,6]naphthyridin-7-yl]-benzene-sulfonamide;
   7-(3-Chloro-2-hydroxy-phenyl)-5-(2,2,2-trifluoro-ethyl)-1,5-dihydro-pyrazolo[4,3-c][1,6]naphthyridin-4-one;
   7-[2-(2-Pyrrolidin-1-yl-ethoxy)-phenyl]-5-(2,2,2-trifluoro-ethyl)-1,5-dihydro-pyrazolo[4,3-c][1,6]naphthyridin-4-one;
   N-{2-[4-Oxo-5-(2,2,2-trifluoro-ethyl)-4,5-dihydro-1H-pyrazolo[4,3-c][1,6]naphthyridin-7-yl]-phenyl}-methanesulfonamide;
   7-(3-Pyrazol-1-yl-phenyl)-5-(2,2,2-trifluoro-ethyl)-1,5-dihydro-pyrazolo [4,3 -c][1,6]naphthyridin-4-one;
   7-(6-Chloro-2-methyl-pyridin-3-yl)-5-(2,2,2-trifluoro-ethyl)-1,5-dihydro-pyrazolo[4,3-c][1,6]naphthyridin-4-one;

N-Isopropyl-4-[4-oxo-5-(2,2,2-trifluoro-ethyl)-4,5-dihydro-1H-pyrazolo[4,3-c][1,6]naphthyridin-7-yl]-benzenesulfonamide;
7-(2-Isopropoxy-pyridin-4-yl)-5-(2,2,2-trifluoro-ethyl)-1,5-dihydro-pyrazolo[4,3-c][1,6]naphthyridin-4-one;
7-(5-Methoxy-pyridin-3-yl)-5-(2,2,2-trifluoro-ethyl)-1,5-dihydro-pyrazolo[4,3-c][1,6]naphthyridin-4-one;
7-(2-Ethoxy-pyridin-3-yl)-5-(2,2,2-trifluoro-ethyl)-1,5-dihydro-pyrazolo[4,3-c][1,6]naphthyridin-4-one;
N,N-Dimethyl-2-[4-oxo-5-(2,2,2-trifluoro-ethyl)-4,5-dihydro-1H-pyrazolo[4,3-c][1,6]naphthyridin-7-yl]-benzenesulfonamide;
N-Ethyl-4-[4-oxo-5-(2,2,2-trifluoro-ethyl)-4,5-dihydro-1H-pyrazolo[4,3-c][1,6]naphthyridin-7-yl]-benzenesulfonamide;
7-[6-(4-Methyl-piperazin-l-yl)-pyridin-3-yl]-5-(2,2,2-trifluoro-ethyl)-1,5-dihydro-pyrazolo[4,3-c][1,6]naphthyridin-4-one;
7-(2-Morpholin-4-yl-phenyl)-5-(2,2,2-trifluoro-ethyl)-1,5-dihydro-pyrazolo[4,3-c][1,6]naphthyridin-4-one;
7-(2-Pyrrolidin-l-yl-pyridin-3-yl)-5-(2,2,2-trifluoro-ethyl)-1,5-dihydro-pyrazolo[4,3-c][1,6]naphthyridin-4-one;
7-(2-[1,4]Diazepan-l-yl-pyridin-3-yl)-5-(2,2,2-trifluoro-ethyl)-1,5-dihydro-pyrazolo[4,3-c][1,6]naphthyridin-4-one;
7-[2-(Ethyl-methyl-amino)-pyridin-3-yl]-5-(2,2,2-trifluoro-ethyl)-1,5-dihydro-pyrazolo[4,3-c][1,6]naphthyridin-4-one;
7-(2-Fluoro-pyridin-3-yl)-5-(2,2,2-trifluoro-ethyl)-1,5-dihydro-pyrazolo[4,3-c][1,6]naphthyridin-4-one;
7-(2-Chloro-pyridin-3-yl)-5-(2,2,2-trifluoro-ethyl)-1,5-dihydro-pyrazolo[4,3-c][1,5]naphthyridin-4-one;
7-Pyridin-2-yl-5-(2,2,2-trifluoro-ethyl)-1,5-dihydro-pyrazolo[4,3-c][1,5]naphthyridin-4-one;
7-Pyridin-4-yl-5-(2,2,2-trifluoro-ethyl)-1,5-dihydro-pyrazolo[4,3-c][1,5]naphthyridin-4-one;
7-[2-(4-Methyl-piperazin-l-yl)-pyridin-4-yl]-5-(2,2,2-trifluoro-ethyl)-1,5-dihydro-pyrazolo[4,3-c][1,5]naphthyridin-4-one;
3-[4-Oxo-5-(2,2,2-trifluoro-ethyl)-4,5-dihydro-1H-pyrazolo[4,3-c][1,5]naphthyridin-7-yl]-pyridine-2-carboxylic acid methyl ester;
7-(6-Amino-pyridin-2-yl)-5-(2,2,2-trifluoro-ethyl)-1,5-dihydro-pyrazolo[4,3-c][1,5]naphthyridin-4-one;
7-(2-Dimethylamino-phenyl)-5-(2,2,2-trifluoro-ethyl)-1,5-dihydro-pyrazolo[4,3-c][1,5]naphthyridin-4-one;
5-(2,2,2-Trifluoro-ethyl)-7-(3-trifluoromethyl-pyridin-2-yl)-1,5-dihydro-pyrazolo[4,3-c][1,5]naphthyridin-4-one;
5-(2,2,2-Trifluoro-ethyl)-7-(5-trifluoromethyl-pyridin-2-yl)-1,5-dihydro-pyrazolo[4,3-c][1,5]naphthyridin-4-one;
3-[4-Oxo-5-(2,2,2-trifluoro-ethyl)-4,5-dihydro-1H-pyrazolo[4,3-c][1,5]naphthyridin-7-yl]-pyridine-2-carbonitrile;
7-(2-Cyclopropylaminomethyl-phenyl)-5-(2,2,2-trifluoro-ethyl)-1,5-dihydro-pyrazolo[4,3-c][1,5]naphthyridin-4-one;
7-(4-Cyclopentyl-pyrimidin-5-yl)-5-(2,2,2-trifluoro-ethyl)-1,5-dihydro-pyrazolo[4,3-c][1,5]naphthyridin-4-one;
7-(5-Chloro-2-methoxy-pyridin-3-yl)-5-(2,2,2-trifluoro-ethyl)-1,5-dihydro-pyrazolo[4,3-c][1,5]naphthyridin-4-one;
7-(3-Methylaminomethyl-pyridin-2-yl)-5-(2,2,2-trifluoro-ethyl)-1,5-dihydro-pyrazolo[4,3-c][1,5]naphthyridin-4-one;
7-(4-Isopropyl-pyrimidin-5-yl)-5-(2,2,2-trifluoro-ethyl)-1,5-dihydro-pyrazolo[4,3-c][1,5]naphthyridin-4-one;
7-(5-Chloro-pyridin-2-yl)-5-(2,2,2-trifluoro-ethyl)-1,5-dihydro-pyrazolo[4,3-c][1,5]naphthyridin-4-one;
7-(3-Chloro-pyridin-2-yl)-5-(2,2,2-trifluoro-ethyl)-1,5-dihydro-pyrazolo[4,3-c][1,5]naphthyridin-4-one;
7-(2-Amino-6-methyl-pyrimidin-4-yl)-5-(2,2,2-trifluoro-ethyl)-1,5-dihydro-pyrazolo[4,3-c][1,5]naphthyridin-4-one;
7-(2-Amino-phenyl)-5-(2,2,2-trifluoro-ethyl)-1,5-dihydro-pyrazolo[4,3-c][1,5]naphthyridin-4-one;
5-(2,2,2-Trifluoro-ethyl)-7-(4-trifluoromethyl-phenyl)-1,5-dihydro-pyrazolo[4,3-c][1,5]naphthyridin-4-one;
7-[2-(2-Hydroxy-ethyl)-phenyl]-5-(2,2,2-trifluoro-ethyl)-1,5-dihydro-pyrazolo[4,3-c][1,5]naphthyridin-4-one;
2-[4-Oxo-5-(2,2,2-trifluoro-ethyl)-4,5-dihydro-1H-pyrazolo[4,3-c][1,5]naphthyridin-7-yl]-nicotinonitrile;
7-(6-Methyl-pyrimidin-4-yl)-5-(2,2,2-trifluoro-ethyl)-1,5-dihydro-pyrazolo[4,3-c][1,5]naphthyridin-4-one;
5-(2,2,2-Trifluoro-ethyl)-7-(6-trifluoromethyl-pyridin-3-yl)-1,5-dihydro-pyrazolo[4,3-c][1,5]naphthyridin-4-one;
7-(3-Amino-pyridin-4-yl)-5-(2,2,2-trifluoro-ethyl)-1,5-dihydro-pyrazolo[4,3-c][1,5]naphthyridin-4-one;
N-{2-[4-Oxo-5-(2,2,2-trifluoro-ethyl)-4,5-dihydro-1H-pyrazolo[4,3-c][1,5]naphthyridin-7-yl]-phenyl}-butyramide;
7-(4-Cyclohexyl-pyrimidin-5-yl)-5-(2,2,2-trifluoro-ethyl)-1,5-dihydro-pyrazolo[4,3-c][1,5]naphthyridin-4-one;
N-{2-[4-Oxo-5-(2,2,2-trifluoro-ethyl)-4,5-dihydro-1H-pyrazolo[4,3-c][1,5]naphthyridin-7-yl]-phenyl}-isobutyramide;
7-(2-Acetyl-phenyl)-5-(2,2,2-trifluoro-ethyl)-1,5-dihydro-pyrazolo[4,3-c][1,5]naphthyridin-4-one;
7-[4-(cyclopropylcarbonyl)phenyl]-5-(2,2,2-trifluoro-ethyl)-1,5-dihydro-4H-pyrazolo[4,3-c][1,5]naphthyridin-4-one;
7-Pyridin-3-yl-5-(2,2,2-trifluoro-ethyl)-1,5-dihydro-pyrazolo[4,3-c][1,5]naphthyridin-4-one; and
3-[4-Oxo-5-(2,2,2-trifluoro-ethyl)-4,5-dihydro-1H-pyrazolo[4,3-c][1,5]naphthyridin-7-yl]-pyridine-2-carboxylic acid;
or an enantiomer, diastereoisomer, or tautomer thereof, or a base or addition salt with an acid of any of the foregoing.

12. A process for preparing a compound of formula (I) or an enantiomer, diastereoisomer, or tautomer thereof or a base or addition salt with an acid of any of the foregoing, according to claim 1, wherein a compound of formula (VII)

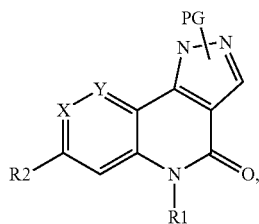

(VII)

wherein PG represents a protecting group, is subjected to a deprotection reaction to obtain a compound of formula (I)

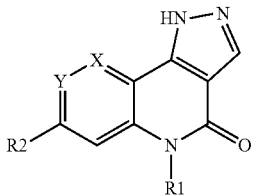

(I)

or an enantiomer, diastereoisomer, or tautomer thereof or a base or addition salt with an acid of any of the foregoing.

13. A process for preparing a compound of formula (I) or an enantiomer, diastereoisomer, or tautomer thereof or a base or addition salt with an acid of any of the foregoing, according to claim 12, further comprising wherein a compound of formula (VI)

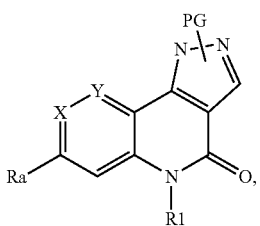

(VI)

wherein PG represents a protecting group and Ra represents a chlorine or bromine atom, and a compound $R_2$-E, wherein E represents a leaving group, are subjected to an organometallic coupling reaction catalyzed with a palladium catalyst to give a compound of formula (VII)

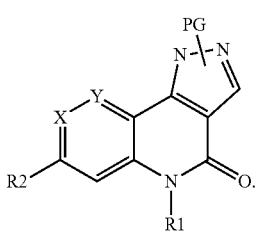

(VII)

14. Process for preparing a compound of formula (I) or an enantiomer, diastereoisomer, or tautomer thereof or a base or addition salt with an acid of any of the foregoing, according to claim 12, further comprising wherein a compound of formula (VI)

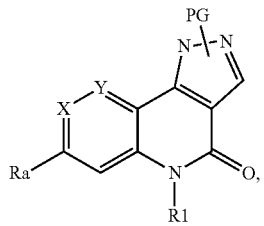

(VI)

wherein PG represents a protecting group and Ra represents a chlorine or bromine atom, is subjected to a coupling reaction, catalyzed with a palladium catalyst, with a diborane derivative to give a boronic acid or ester of formula (VIII)

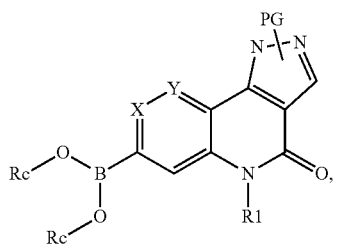

(VIII)

wherein PG represents a protecting group and Rc is a hydrogen atom or the two groups Rc are each a carbon atom and are bonded together, and are non-substituted or substituted with one or more ($C_1$-$C_4$)alkyl group, and the compound of formula (VIII) is subjected to a Suzuki coupling reaction catalyzed with a palladium catalyst with a compound $R_2$-E, wherein E represents a leaving group, to give a compound of formula (VII)

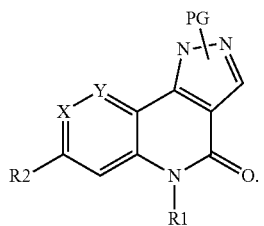

(VII)

15. A compound of formula (VII)

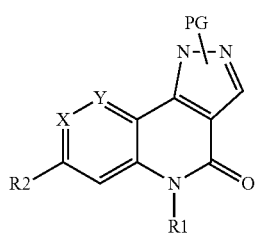

(VII)

wherein X is CH or a nitrogen atom;
Y is CH or a nitrogen atom,
wherein X or Y is a nitrogen atom;
$R_1$ is a ($C_1$-$C_4$)alkyl, wherein the ($C_1$-$C_4$)alkyl is non-substituted or substituted with one or more halogen atoms;

$R_2$ is an aryl or a heteroaryl group, wherein the aryl or heteroaryl group is non-substituted or substituted with one or more substituents independently selected from the group consisting of:
a halogen atom,
a $(C_1-C_4)$alkyl group, wherein the alkyl group is non-substituted or substituted with one or more substituents independently selected from the group consisting of a halogen atom, heterocyclyl, $(C_1-C_4)$alkoxy, hydroxy group, and $NHR_3$,
O—$R_4$,
$(CO)NR_5R_{5'}$,
a heterocyclyl group, wherein the heterocyclyl group is non-substituted or substituted with one or more $(C_1-C_4)$alkyl group,
a cycloalkyl group,
a cyano group,
$NR_6R_{6'}$,
$SO_2NR_6R_{6'}$,
$NHSO_2R_7$,
$NH(CO)R_7$,
$(CO)R_8$, and
a heteroaryl group; and
PG represents a protecting group.

16. A pharmaceutical composition comprising a compound according to claim 1, or an enantiomer, diastereoisomer, or tautomer thereof or a pharmaceutically acceptable salt of any of the foregoing, and at least one pharmaceutically acceptable excipient.

17. A method for inhibiting MetAP2 comprising administering an effective amount of a compound, or an enantiomer, diastereisomer, or tautomer thereof, or a base or addition salt with an acid of any of the foregoing, according to claim 1.

18. The compound of claim 15, wherein the PG is 2-(trimethylsilyl)ethoxy]methyl (SEM) or tetrahydropyranyl (THP).

* * * * *